(12) United States Patent
Lazarovich

(10) Patent No.: US 10,842,433 B2
(45) Date of Patent: Nov. 24, 2020

(54) METHODS AND SYSTEMS USING CONDITIONING FOR PAIN MINIMIZATION

(71) Applicant: REMmedy, Inc., Stowe, VT (US)

(72) Inventor: Mark Lazarovich, Stowe, VT (US)

( * ) Notice: Subject to any disclaimer, the term of this patent is extended or adjusted under 35 U.S.C. 154(b) by 0 days.

(21) Appl. No.: 16/687,738

(22) Filed: Nov. 19, 2019

(65) Prior Publication Data

US 2020/0237297 A1 Jul. 30, 2020

Related U.S. Application Data

(60) Provisional application No. 62/798,659, filed on Jan. 30, 2019.

(51) Int. Cl.
*A61B 5/00* (2006.01)
*A61M 21/00* (2006.01)
(Continued)

(52) U.S. Cl.
CPC ........ *A61B 5/4824* (2013.01); *A61B 5/02405* (2013.01); *A61B 5/02444* (2013.01);
(Continued)

(58) Field of Classification Search
CPC ........................ A61M 21/00–02; A61B 5/4824
See application file for complete search history.

(56) References Cited

U.S. PATENT DOCUMENTS 5,023,020 A 6/1991 Machida et al.
5,318,503 A 6/1994 Lord
(Continued)

FOREIGN PATENT DOCUMENTS

WO 2018108582 5/2018

OTHER PUBLICATIONS

Tanaka et al, "Statistical Features of Hypnagogic EEC Measured by a New Scoring System", 1976; Sleep, 19(9): 731-738.

*Primary Examiner* — Thaddeus B Cox
(74) *Attorney, Agent, or Firm* — Caldwell Intellectual Property Law

(57) ABSTRACT

A system for inducing a Pavlovian association of a scent with a state of less-than-moderate pain, to thereby minimize perceived pain, and to reduce the need for narcotic analgesics. The system includes at least a physiological sensor configured to detect at least one physiological parameter of the user. The physiological parameter of the user may include heart rate variability, blood pressure, galvanic skin response, movement, facial expression and the like. After detection of the physiological parameter, an activation signal is then transmitted to an automatically activated scent diffuser, which diffuses a scent, as a function of the electronic activation signal. The scent may include one or more scent liquids, such as perfumes, essential oils, or the like. Activation of the scent diffuser is maintained by a control circuit that receives the detection signal from the at least one physiological sensor, ascertains that the user has transitioned to a state of less-than-moderate pain, and transmits a signal to the automatically activated scent diffuser. After an association, wherein association further includes conditioning, is created in the user, by iterative performance of the foregoing steps, the user can manually activate a second scent source, in order to trigger a conditioned reflex to assist the user in reducing pain levels.

22 Claims, 13 Drawing Sheets

(51) Int. Cl.
  *A61B 5/024* (2006.01)
  *A61L 9/12* (2006.01)
  *A61B 5/11* (2006.01)
  *A61B 5/053* (2006.01)

(52) U.S. Cl.
  CPC .............. *A61B 5/0533* (2013.01); *A61B 5/11* (2013.01); *A61L 9/12* (2013.01); *A61M 2021/0016* (2013.01)

(56) References Cited

U.S. PATENT DOCUMENTS

| | | |
|---|---|---|
| 6,702,767 B1 | 3/2004 | Douglas |
| 6,866,041 B2 | 3/2005 | Hardy, Jr. et al. |
| 9,434,907 B2 | 9/2016 | Jeon et al. |
| 9,511,166 B1 | 12/2016 | Li |
| 9,839,762 B2 | 12/2017 | Berg et al. |
| 2005/0185398 A1 | 8/2005 | Scannell, Jr. |
| 2007/0207220 A1 | 9/2007 | Luedtke et al. |
| 2010/0309434 A1 | 12/2010 | Van Schijndel et al. |
| 2011/0015500 A1 | 1/2011 | Wu |
| 2011/0160619 A1 | 6/2011 | Gabara |
| 2015/0190607 A1 | 7/2015 | Sugio et al. |
| 2015/0290419 A1 | 10/2015 | Kare et al. |
| 2017/0053068 A1 | 2/2017 | Pillai et al. |
| 2017/0312476 A1 | 11/2017 | Woo |
| 2017/0319816 A1 | 11/2017 | Sokol et al. |
| 2017/0361133 A1 | 12/2017 | Yu et al. |
| 2018/0050171 A1 | 2/2018 | Tabert et al. |
| 2018/0125256 A1 | 5/2018 | Tsern et al. |
| 2018/0261332 A1* | 9/2018 | Baeuerle ................ G06Q 50/22 |
| 2018/0296794 A1* | 10/2018 | Clark .................... A61M 21/02 |

* cited by examiner

METHODS AND SYSTEMS USING CONDITIONING FOR PAIN MINIMIZATION

CROSS-REFERENCE TO RELATED APPLICATIONS

This application claims the benefit of priority of U.S. Provisional Patent Application Ser. No. 62/798,659, filed on Jan. 30, 2019, and titled "METHODS AND SYSTEMS OF A PAVLOVIAN PAIN-FREE STATE," the entire content of which is hereby incorporated by reference.

FIELD OF THE INVENTION

The present invention generally relates to the field of technologies to aid in pain relief with less use of medications, particularly opiates. In particular, the present invention is directed to methods and systems for using Pavlovian conditioning to help patients or users, experiencing pain, shorten their reliance on medications during management of their pain.

BACKGROUND

Pain relief after surgery and hospital admissions because of accidents is generally treated with powerful narcotics and opiates such as oxycodone, morphine, and fentanyl. These medications prove very useful in reducing and eliminating pain within minutes of administration. While highly effective, these medications are highly addictive, with the US National Institute on Drug Abuse (NIDA) estimating that approximately 21 to 29 percent of patients to whom opioids are prescribed, for chronic pain, misuse the opioids. Medical professionals have tried to reduce the number of patients prescribed opioids by prescribing less powerful medications as well as by creating systems to provide monitoring by pharmacists to verify that prescriptions for such medications have not been refilled early or mishandled. However, for patients recovering from major surgeries, accidents, or with chronic pain conditions such as fibromyalgia, using less powerful medications provides inadequate pain relief. Patients may still feel intense pain that may be unbearable, and may still report high levels of pain, also called "pain scores."

SUMMARY OF THE DISCLOSURE

Therefore, in order to minimize reliance upon opioid painkillers while still providing relief from pain, I have developed a method and system which creates a Pavlovian association between transition from a state of severe or moderate pain to a state of mild or no (less-than-moderate) pain, and a particular scent. By detecting this transition, using one or more physiological parameters of the user, and activating an automatically activated scent diffuser located near the user, one conditions the user, upon subsequent perception of the same scent, to experience relief from pain. Once the association has been created, one can trigger the association by manually releasing the same scent. This manual release can be done, using a manually actuated scent diffuser or, even more simply, by opening a package containing a scent-producing material. The user thus experiences the same degree of pain relief, with a shorter duration of opioid use or by use of less powerful non-narcotic painkillers. For example, a treatment plan for a patient who recently had surgery to repair a fracture may be to bring down the level of pain the patient is experiencing into the pain range 0-3 on the 11-point Numeric Rating Scale (NRS), so that the pain ceases to interfere with falling asleep. Patients, who are able to sleep in the hospital, heal faster and can be discharged sooner, with less risk of subsequent adverse outcomes.

These and other aspects and features of non-limiting embodiments of the present invention will become apparent to those having ordinary skill in the art, upon review of the following description of specific non-limiting embodiments of the invention, in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

Figure 1:
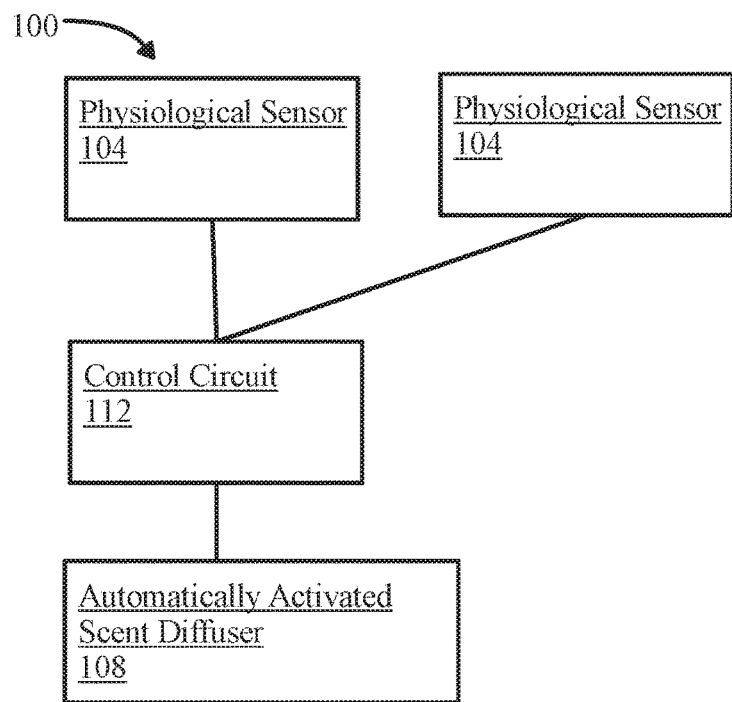
FIG. 1 is a block diagram illustrating an exemplary embodiment of a system for inducing a Pavlovian association of a scent with a pain-free state.

The drawings are not necessarily to scale and may be illustrated by phantom lines, diagrammatic representations and fragmentary views. In certain instances, details, that are not necessary for an understanding of the embodiments or that render other details difficult to perceive, may have been omitted.

DETAILED DESCRIPTION

Medical professionals in North America typically employ an 11-point Numeric Rating Scale (NRS-11) for rating of pain experienced by a patient whose age is 10 years or older. On the scale, the level 0 represents no pain. Levels 1-3 represent "mild" pain which interferes little with Activities of Daily Living ("ADLs"). Levels 4-6 represent "moderate" pain which interferes significantly with ADLs. Levels 8-10 represent "severe" pain which renders the patient disabled, in other words, unable to perform ADLs. For consistency, pain measuring devices, used with patients under age 10 or those unable to self-report, for example, patients under anesthesia or stroke victims, use the same numeric scale to report to doctors and nurses. Treatment goals for a post-surgical patient typically include getting pain levels down into the "mild" range, so that the patient can perform ADLs and can be sent home from a hospital, preferably without becoming addicted to an opioid. A typical approach is to taper down a dosage of painkiller on successive days, so that a non-opioid painkiller can replace any opioid initially used. This desired scenario is complicated by the fact, that an initial high level of pain may stress the patient and/or interfere with the patient's ability to sleep. Stress and exhaustion tend to raise the level of pain which a patient perceives. Helping a patient to de-stress and to sleep are thus important parts of a successful treatment plan or regimen. Effective non-pharmacological solutions to these problems are needed. See the review article by Raymond Sinatra MD of Yale, "Causes and Consequences of Inadequate Management of Acute Pain," in Pain Medicine 11: 1859-1871 (2010). Hypnosis has been tried but is ineffective for persons in the so-called "low suggestible" category. Even with "high suggestibles" and "medium suggestibles" fewer than half the patients find that hypnosis effectively treats their perceived pain. See Thompson et al., Neurosci. Biobehay. Rev., 99:298-310 (April 2019).

At a high level of generality, aspects of the present disclosure are directed to systems and methods for creating a Pavlovian association between perception of a particular scent and a transition down to a state of less-than-moderate pain (level 3 or less). At least a physiological sensor may detect one or more physiological parameters of a user, which may be used by a control circuit, such as a microprocessor or mobile device, to identify when a user is beginning to experience a state of less-than-moderate pain. In an embodiment, heart rate variability ("HRV") measurements may be indicative of when a user begins to experience a state of less-than-moderate pain. A control circuit may cause a scent diffuser to release a scent upon detection, which user may smell as user begins to experience a state of less-than-moderate pain, that is, as a transition from a higher level of pain to mild or no pain is accomplished. Optionally, HRV measurements can also be used to detect the prior, higher, level of pain. For example, a treatment plan may include giving a dose of painkiller to a patient each evening at bedtime, while measuring the patient's pain level. By iteratively releasing the same scent each time, as the painkiller becomes effective ("kicks in"), the patient is conditioned to associate that scent and relief from pain (the transition). Perceiving the scent creates a conditioned reflex of pain relief, so the patient user tends to relax, which speeds a transition to a level of less-than-moderate pain and enables the patient user to more easily fall asleep normally.

After creation of the association, wherein association further includes conditioning, a kit including a user-activated scent diffuser device or other scent source may then be used by the user (for example at home) to assist in pain management after surgery, accidents, and/or as part of a treatment plan to assist in management of a chronic pain disorder such as fibromyalgia, migraines, cancer pain, Lyme disease, arthritis, neurogenic pain, pelvic pain, headaches, low-back pain, rheumatoid arthritis, multiple sclerosis, lupus, endometriosis, and shingles. Since the association, wherein association further includes conditioning, has already been created, and automatic sensing of a pain level is no longer needed, a kit including a user-activated scent diffuser need not communicate with sensors or other equipment to work, so the user may be able to carry it anywhere, and use it under any circumstances in which the user experiences pain.

Referring now to FIG. 1, an exemplary embodiment of a system 100 for including a Pavlovian association of a scent with a state of less-than-moderate pain is illustrated. System 100 includes at least a physiological sensor 104. At least a physiological sensor 104 may be any device or component that measures a physiological parameter of a user and generates an electrical signal as a function of the measurement. At least a physiological parameter may include any information that may be sensed from a user's body, including without limitation any electrical, chemical, optical, auditory, olfactory, kinetic, or other information; at least a physiological parameter may include, without limitation, galvanic skin response or skin conductance response, pulse rate, breathing rate, blood flow, heartbeat signatures, electrolyte type and/or concentration, blood metabolite levels or ratios, blood pH level, position and/or balance, body strain, neurological functioning, brain activity, brain waves, blood pressure, cranial pressure, hydration level, auscultatory information, skin and/or core body temperature, facial emotions, eye muscle movement, body movement, blood volume, inhaled and/or exhaled breath volume, exhaled breath physical and/or chemical composition, reflex response sleepiness, response to external stimuli, swallowing volume, swallowing rate, head position or tilt, internal body sounds, functional near-infrared spectroscopy signals, snoring, and/or other physiological information. Various non-limiting examples of such parameters are described in further detail in this disclosure with regard to exemplary categories and/or embodiments of at least a physiological sensor 104.

With continued reference to FIG. 1, at least a physiological sensor 104 may include, without limitation, at least an electrophysiologic sensor, defined herein as a sensor that detects at least an electrical, magnetic, or electromagnetic parameter, state, or reading regarding the body of the user. At least an electrophysiologic sensor may include an electrodynamic sensor device configured to sense an electrical activity of the heart of a subject. For example, the electrodynamic sensor may be configured to sense a heart rate or heart rate variability (HRV) pattern using electrical activity of the heart, for instance using electrocardiography (ECG or EKG), or conductivity. Electrocardiography may include a process of recording electrical activity of a heart over a period of time using electrodes placed on the skin; electrodes may detect tiny electrical changes on the skin that arise from a heart muscle's electrophysiologic pattern of depolarizing during each heartbeat. ECG or EKG may be categorized based on the number of electrodes placed on the skin. For example, a 12-lead ECG may gather readings from 12 different areas of the heart. A 10-lead ECG may gather readings from 10 different areas of the heart. An ECG may be used to measure rate and rhythm of heartbeats or other patterns relating to heartbeats, including without limitation heart rate variability patterns. Electrodes may be placed in contact with user's skin using any suitable means, including adhesion or incorporation in a wearable device such as a band of elastic material around user's torso, that places electrodes in contact with user's skin. In some embodiments, direct contact may not be necessary, and electrical functioning may be monitored capacitively, inductively, electromagnetically, or a combination of these approaches. In some embodiments, ECG or EKG may allow for continuous tracking and heart rate monitoring. In some embodiments, heart rate monitoring with ECG or EKG for example, may be performed on a user at rest such as when user is sitting or lying down, and/or when a user is exercising, such as walking on a treadmill at an incline. In an embodiment, at least an electrophysiologic sensor may include a Holter monitor. A Holter monitor may include wearable device such as a lanyard around a user's neck, that records a continuous ECG for a period of time, sometimes ranging from 24 to 48 hours. In an embodiment, a Holter monitor may include wires from electrodes that are placed on a user's chest, and which are connected to a battery-operated recording device worn around a user's neck, belt, or shoulder strap. A Holter monitor may record electrical readings of the heart continuously for a set duration of time. In an embodiment, heart rate monitoring with ECG or EKG for example, may be performed using an event monitor. An event monitor may include a device similar to a Holter monitor, but it may not record continuously as a Holter monitor would, but rather may record only at certain times of the day and/or for certain periods of time, and in some instances, recording may be prompted by a user. An event monitor may contain a record button when a user may experience symptoms at which point sensors may become activate and start recording electrical activity. For example, in an embodiment, a user may wear an event monitor, and when user begins to experience pain, user may record user's heart rate activity. When user experiences a state of less-than-moderate pain, user may also record user's heart rate activity, so that comparisons to electrical activity in each state can be examined. Persons having ordinary skill in the pain monitoring art, upon reviewing the entirety of this disclosure, will be aware of various ways in which EKG data may be collected, consistently with the instant disclosure. See, for example, U.S. Pat. No. 8,512,240 granted 2013 Aug. 20 to Zuckerman-Stark & Kliger, assigned Medasense Biometrics Ltd.

With continued reference to FIG. 1, at least an electrophysiologic sensor may include a wearable device which includes an electrodynamic sensor device configured to sense an electrical activity of the heart of a subject. Wearable device may include for example, an electrophysiologic sensor worn around a user's neck, waistband, placed in a user's pocket, on a user's wrist and/or on a user's appendage. For example, electrophysiologic sensor may be contained within a wristwatch worn on a user's wrist, such as the APPLE WATCH, series 4 or series 5, as produced by Apple of Cupertino, Calif., which contains electrodes that come into contact with the skin and are able to detect and record a user's heart rate activity and electrical impulses. Electrophysiologic sensor may include a Holter monitor worn on a lanyard around the neck, and/or worn around a user's belt that contains electrodes that come into contact with the skin. In an embodiment, Holter monitor may be worn as a backpack on a user's back, which contains electrodes that come into contact with user's skin at various points along user's body. In an embodiment, electrophysiologic sensor may be contained within a ring worn on a user's finger, such as the MOTIV RING as produced by Motiv Inc. of San Francisco, Calif., and the OURA RING as produced by OuraRing Inc of San Francisco, Calif. 94127. In an embodiment, at least a physiological sensor may include a device worn as a strap around a user's chest, such as a chest strap monitor.

With continued reference to FIG. 1, at least an electrophysiologic sensor may include a sensor that monitors neurological functioning. As a non-limiting example, electrophysiologic sensor may include one or more sensors that perform an electroencephalogram (EEG); EEG may involve detection of patterns, such as brainwaves, otherwise known as neural oscillations. EEG may be performed by detection of electrical patterns in neural activity using electrodes contacting user's cranium, such as electrodes placed along a forehead of user. Electrodes may be adhered to user or incorporated in a wearable device, such as without limitation an earpiece or item of headgear placing electrodes at cranial locations such as a forehead or temple. In some embodiments, direct contact may not be necessary, and neurological functioning can be monitored capacitively, inductively, electromagnetically, or a combination of these approaches. In some embodiments, brain waves may couple with low frequency acoustical sensors integrated into a head-mounted module, or the like. In some embodiments, monitoring may be performed continuously for a set duration of time, such as in a 24-48-hour continuous interval, such as when a user is monitored remotely from home. In some embodiments, monitoring may be for a particular window of time such as, for example, a 3-hour period of time while a user is monitored under the supervision of a medical professional. Persons having ordinary skill in the art, upon reviewing the entirety of this disclosure, will be aware of various ways in which EEG data may be collected, consistently with the instant disclosure.

Continuing to view FIG. 1, at least an electrophysiologic sensor may include a sensor configured to perform an electrooculogram (EOG); EOG may be defined as an electrophysiologic measurement of eye motion. EOG may be collected using electrodes mounted at or near user's eyes, for instance through use of a mask or other wearable device that contacts the user's eyelids or rests nearby. EOG may be detected through contactless means such as capacitive, inductive, or electromagnetic detection. Alternatively or additionally, at least an electrophysiologic sensor may include electrodes or other sensors for monitoring an electromyogram (EMG) signal measuring electrical activity of muscles or muscular tissue of a user. At least an electrophysiologic sensor may include an electrodermal activity (EDA) sensor, also known as skin conductance, galvanic skin response (GSR) sensor, electrodermal response (EDR) sensor, or the like, which may measure continuous variation in electrical characteristics of skin. GSR sensors may include one or more sensors that detect changes in electrical activity resulting from changes in sweat gland activity. Electrodes may be placed on the skin to detect and transmit such changes. GSR sensors may contain silver and/or silver-chloride contact points with a user's skin. A signal may be sent through an electrode to the contact point with a user's skin whereby data is then gathered and transmitted to the GSR sensor. Signals transmitted to a user may range between 1-10 Hertz. In an embodiment, increased sympathetic nervous system activity may be correlated with bodily indicators of arousal of the sympathetic nervous system such as increased heart rate, blood pressure, and sweating. In an embodiment, increased parasympathetic nervous system activity may be associated with bodily indicators of arousal of the parasympathetic nervous system such as decreased heart rate, blood pressure, and sweating. In an embodiment GSR response may be measured by placing two electrodes on a user's body. A low constant voltage may then be applied, whereby a voltage difference between the two electrodes may then be measured. Skin conductance may then be measured and reported. For example, electrodes may be placed on two fingers, both hands, and/or both feet.

With continued reference to FIG. 1, at least a physiological sensor 104 may include one or more sensors configured to detect facial expression. For instance and without limitation, one or more sensors may be configured to detect movement and expression of facial nerves and muscles that may indicate a user's sympathetic and parasympathetic response to a stimulus. At least a physiological sensor may include a facial electromyography which may track the activity of facial muscles with electrodes attached to the surface of a user's skin. In an embodiment, facial electromyography may detect and amplify electrical impulses generated by muscle fibers during contraction. Facial electromyography may place electrodes on a user's face at locations near major muscle groups, including locations near the left or right Corrugator Supercilia and the left or right Zygomaticus. Facial expressions detected by facial electromyography may be categorized by the Facial Action Coding System (FACS) which represents a standardized classification system of facial expressions based on anatomic features. Expressions and anatomic features may provide insight into a user's emotional state and thus overall pain state. For example, an image of a user, whose mouth corners are pulled upward, indicates that a user is smiling and thus not experiencing pain.

Still viewing FIG. 1, at least a physiological sensor 104 may include one or more sensors configured to detect arterial or vascular data. For instance, and without limitation, at least a physiological sensor 104 may include a photoplethysmography (PPG) sensor, which may sense the body's rate of blood flow using a light-based technology whereby a light source is emitted through or at tissue containing blood vessels, and light reflected by or transmitted through the tissue is measured. At least a physiological sensor 104 may include an impedance plethysmograph for measuring changes in volume within an organ or body (usually resulting from fluctuations in the amount of blood or air it contains). For example, an impedance plethysmograph to monitor blood pressure in real-time. At least a physiological sensor 104 may include a sensor to detect pulse oximetry, where pulse oximetry is a standard noninvasive technique of estimating blood gas levels. Pulse oximeters typically employ two or more optical wavelengths to estimate the ratio of oxygenated to deoxygenated blood. Similarly, various types of hemoglobin, such as methemoglobin and carboxyhemoglobin may be differentiated by measuring and comparing the optical absorption at key red and near-infrared wavelengths. See Lopez-Martinez et al, "Pain Detection with fNIRS-Measured Brain Signals," arXiv:1907.12830v1 (2019 Jul. 30). The term "fNIRS" is an acronym for "functional near-infra-red spectroscopy." Additional wavelengths may be incorporated and/or replace conventional wavelengths. For example, by adding additional visible and infrared wavelengths, myoglobin, methemoglobin, carboxyhemoglobin, bilirubin, $SpCO_2$, and blood urea nitrogen (BUN) may be estimated and/or monitored in real-time in addition to the conventional pulse oximetry. At least a physiological sensor 104 consisting of a pulse oximeter may include a sensor, attached to a user's finger, which measures blood saturation directly on contact with the skin. In an embodiment, the pulse oximeter may include a portable, battery-operated device that can be used remotely by a user, without direct medical supervision.

With continued reference to FIG. 1, at least a physiological sensor 104 may monitor blood pressure, using, as a non-limiting example, a digital blood pressure monitor; digital blood pressure monitor may include actuators and sonic and pressure transducers placed on the skin, and may measure systolic and/or diastolic pressure, for instance by monitoring a pressure at which a "Korotkoff sound" is first heard (systolic), then disappears (diastolic). This technique may also be used to monitor intra-cranial pressure and other internal pressures. Blood pressure may also be measured by comparing the time between pulses at different regions of the body. At least a physiological sensor 104 may alternatively or additionally include pyroelectric sensor for monitoring heart rate, heart rate variability patterns, pulse, pulse variability patterns and the like.

Still referring to FIG. 1, at least a physiological sensor 104 may include a body temperature sensor, which may be any sensor that acquires a temperature of user's body or a portion thereof. Temperature sensor may include, without limitation one or more infrared sensors, which may be composed of thermoelectric/pyroelectric materials or semiconductor devices, such as photodiodes or photoconductors, thermistors, thermocouples, or any other elements or components used in digital and/or electric thermometers or other temperature sensors. Temperature sensor may detect a skin temperature at one or more locations on user's body. Temperature sensor may contact user, or may detect user temperature remotely, for instance by capturing infrared radiation.

Continuing to refer to FIG. 1, at least a physiological sensor 104 may include at least a motion sensor. At least a motion sensor may include at least a gyroscope, which may detect orientation changes of the at least a gyroscope; multiple gyroscopes may detect orientation changes with respect to multiple axes, such as three gyroscopes to detect orientation changes with respect to three axes of rotation, or the like. At least a motion sensor may include at least an accelerometer, such as one or more microelectromechanical systems (MEMS) devices. An accelerometer may measure acceleration or position in two or more axes; alternatively or additionally, at least an accelerometer may include a plurality of accelerometers to detect acceleration with respect to a plurality of axes, such as without limitation three accelerometers that detect motion with regard to three dimensional axes. At least a motion sensor may include an inertial measurement unit (IMU), which may include multiple types of motion sensors in a single chip or system. At least a motion sensor may be mounted to one or more parts of user's body to detect motion thereof. Changes in patterns in user motion may indicate a transition by user from a pain-state to a pain-free state; for instance, a transition from a pain-state to a pain-free state may be accompanied by decrease in or cessation of movement by user, and/or by an increased regularity of chest movements indicating regular breathing.

As a further non-limiting example, and still referring to FIG. 1, at least a physiological sensor 104 may include at least a camera. At least a camera may be any electronic device capable of capturing light, whether in visible or non-visible spectra, and transmitting an electrical signal based on the detection. At least a camera may, as a non-limiting example, capture an eye area of user may be captured by a camera to determine whether or not an eye movement occurs based on the analysis of the captured images; when the eye rapidly moves such as for example when a user enters REM sleep, user may be entering a pain-free state, whereas users experiencing a pain-state may be unable to achieve such a state. Camera may detect body movement of user, which may be used similarly to body movements detected by at least a motion sensor; camera may, for instance, capture a sequence of images of user's body and compare images of the sequence of images to determine whether user has moved user's body, and if so, how frequently or to what extent. Camera may detect mobility of user, such as for example when a user is first mobile after surgery. Camera may detect if a user is immobile, such as for example when a user is lying in a bed in a recovery room immediately after undergoing surgery or is immobile because a user is intubated and receiving treatment in the intensive care unit.

Continuing to refer to FIG. 1, at least a physiological sensor 104 may include at least an acoustic sensor, such as a microphone or the like. At least an acoustic sensor may detect and/or monitor breathing characteristics of user, for instance via auscultatory signal extraction. In an embodiment, an acoustic sensor may be used to sense sounds associated with breathing. Signal processing algorithms may then be used to extract breathing sounds from other sounds and noise, for instance using digital signal filtering or noise elimination processes. This information may be used, as a non-limiting example, to measure and/or track intensity, volume, and speed of breathing, which may in turn be used to determine a user's state of wakefulness, pain-state, or pain-free state. Alternatively or additionally, at least a physiological sensor 104 may monitor breathing, using pressure transducers. For instance, and without limitation, changes in pressure inside or near the ear associated with breathing may be measured directly and, through signal processing, translated into a breathing monitor. Similarly, optical reflection sensors may be used to monitor pressure by monitoring physical changes in the skin or tissues in response to breathing. For monitoring the physical changes of the tympanic membrane in response to breathing, and hence ascertaining breathing rate, an optical signal extraction approach may be employed. As a further non-limiting example, microphones positioned correctly near a sleep surface can sometimes pick up and detect a heartbeat and respiration. Microphones may also hear user's complaints that user is unable to sleep because of pain-state, and/or hear that user was silent because user was in a pain-free state and thus was able to sleep uninterruptedly. Microphones may also be utilized to detect user's pain response, such as, for example, when a user complains to a medical professional such as a nurse or doctor or caregiver that user is in pain. Microphone may also be utilized to detect user's lack of complaint, such as when user may not complain about user's pain state because user's pain is adequately managed and/or absent.

With continued reference to FIG. 1, at least a physiological sensor 104 may include at least a dolorimeter. At least a dolorimeter may include an instrument that may provide measurements indicating a user's pain threshold and/or pain tolerance. Pain threshold may include a point along a curve of increasing perception of a stimulus at which point pain begins to be felt by a user. Pain tolerance may include a maximum level of pain that a user is able to tolerate. At least a dolorimeter may apply steady pressure, heat or electrical stimulation to an area on a user's body. In some instances, at least a dolorimeter may move a joint or other body part of a user. Pressure, heart, electrical stimulation, and/or movement may assist a clinician in determining what kind of input induces a sensation of pain. For example, a user who has just had a hip replacement surgery, may receive from at least a dolorimeter an electric stimulation twenty-four hours after surgery to see if a patient responds to such input. Complaints of pain or immediate jerking or pulling away by a user from at least a dolorimeter may indicate the presence of pain and that a user may be experiencing a pain state. Lack of complaint and/or jerking or pulling away by a user from at least a dolorimeter may indicate lack of presence of pain. At least a dolorimeter may include physiological sensors that may detect pain or lack of pain at different locations on the body and/or through touchless technology. In an embodiment, at least a dolorimeter may include for example, any of the medical monitoring systems as manufactured by Mdoloris Medical Systems of Loos, France. This may include for example, the use of heart rate readings derived from EKG leads to monitor pain levels of a user. In an embodiment, at least a dolorimeter may include the use of a single sensor to detect multiple physiological states such as for example the PMD-200 as produced by Medasense Biometrics Ltd. of Okafim, Israel; see U.S. Pat. No. 8,512,240. This may include for example, a sensor placed on a user's finger that uses photoplethysmography and an accelerometer to monitor heart rate, heart rate variability, galvanic skin response, and temperature. In an embodiment, at least a physiological sensor may be contact-free with a user such as a piezo electric sensor placed under a user's mattress. This may include for example, EARLYSENSE SYSTEM, INSIGHT SYSTEM, and OEM-INTEGRATION SOLUTIONS as produced by EarlySense of Ramat Gan, Israel. Contactless sensors may provide continuous monitoring of physiological parameters such as for example, heart rate, heart cardio ballistic effect, respiratory rate, and/or movement.

Still referring to FIG. 1, at least a physiological sensor 104 is configured to detect at least a physiological parameter of user and transmit a detection signal. Detection signal may be transmitted via wired connection to one or more other elements of system 100 as described below; for instance, and without limitation, at least a physiological sensor 104 may be incorporated in a single electronic device, or mounted on a single chip, with one or other additional components of system 100. Alternatively or additionally, detection signal may be transmitted to one or more components of system 100 wirelessly. For instance, and without limitation, at least a physiological sensor 104 may include one or more wireless transceivers, which may communicate according to protocols such as BLUETOOTH®, Wi-Fi, or ZigBee and may be configured to transmit information wirelessly one or more other components of system 100.

Continuing to refer to FIG. 1, system 100 includes an automatically activated scent diffuser 108. Automatically activated scent diffuser 108 is configured to receive an electronic activation signal and diffuse a scent in response to the electronic activation signal; the automatically activated scent diffuser 108 may be any device that can selectively release a scent into the air, so that user can smell the scent. Scent diffuser may include a scent source, which may include a material that releases scent molecules into the air. Scent molecules may include any molecules that human olfactory receptors detect as having an aroma. Scent molecules may pass through air to a user's nose by diffusion. Scent molecules may have aromas recognizable to users; aromas may include aromas generally considered pleasant, such as the aromas of fruits, flowers, herbs, pine needles, or the like. Scent source may include a material containing one or more volatile materials that either have the desired aroma or carry molecules having the desired aroma in solution. Scent source may include one or more scent wafers, which may release scent upon exposure to air, for instance by evaporation of volatile materials contained within scent wafer. Scent source may include one or more scent liquids, such as perfumes, essential oils, or the like; scent liquids may be volatile, or contain volatile materials, causing diffusion through evaporation. Scent-diffusing material may include a gas. The scent source may be in any other suitable form, including a film, foam, or gel. The scent source may include a material that releases scent molecules under specific circumstances; for instance, the scent source may include a wafer, film, liquid, or other material that releases scent only on exposure to heat, electric current, or the like. As a non-limiting example, the scent source may contain a mixture or solution of volatile or scent-diffusing material with a substance that seals the scent-diffusing material at a first temperature, such as room temperature, but changes to release scent-diffusing material at a second temperature, which may be a higher temperature; substance may be waxy, may have a structure that encapsulates scent-diffusing material in small envelopes or capsules of material that will open or rupture upon exposure to heat, or may combine with scent-diffusing material via chemical bonds that release upon heat exposure. Alternatively or additionally, substance may be a material that encapsulates or maintains a chemical bond to scent-diffusing material until exposed to an electric current or field. In an embodiment, removal of a release stimulation may result in a cessation of diffusion of scent; for instance, where substance encapsulates scent-diffusing material until exposure to ultrasonic vibration, heat or electric currents and/or fields, cessation of heat, ultrasonic vibration, or electric currents and/or fields may cause substance to re-encapsulate scent-diffusing material. Similarly, chemical bonds that are separated by heat, ultrasonic vibration, and/or electric current and/or fields may reform upon cooling or cessation of the electric stimulus. Heat used to release scent-diffusing material may be applied using an electrical heating element, which may be controlled by a control circuit 112, microprocessor, microcontroller, or the like; electric current and/or field may be similarly provided electrically. Ultrasonic vibration may be applied using any electrically triggered sonic vibration generating component, such as without limitation piezoelectric vibrating components. The automatically activated scent diffuser may be located near user's head and/or nose, near olfactory sensory neurons located in the olfactory epithelium. Odorants may penetrate into the olfactory epithelium and mix with mucus which acts as a solvent for odor molecules, and is constantly replaced, approximately every 10 minutes.

Still viewing FIG. 1, scent-diffusing material may be contained in an enclosed container and selectively released. For instance, where scent-diffusing material includes a liquid or gel, scent-diffusing material may be contained in a cartridge, compartment, or bottle-like component that may be sealed until release is desired. Where scent-diffusing material includes a film, foam, or solid object such as a wafer, scent-diffusing material may be stored in a cartridge, wrapper, or compartment that may be selectively opened when scent diffusion is desired. A scent-diffusing gas may similarly be contained in a cartridge or compartment; scent-diffusing gas may be contained under pressure. Selective opening of enclosed container may include piercing a wrapper, opening a selectively closable aperture, or the like. Alternatively or additionally, liquid, gas, or gel may be released from one or more nozzles, such as spray nozzles; nozzles may be mechanically or electrically actuated in any suitable way, including forcing of scent-diffusing material through nozzles using a pump, impeller, or other pressure source, including pressurized cartridges. Nozzles may be actuated by opening a valve. An aperture of enclosed container may be opened by electrically controlled mechanical movement of a door or lid, for instance using an electric motor or linear actuator, a servo, or the like.

Continuing to view FIG. 1, automatically activated scent-diffuser may include one or more dispersal mechanisms. Where nozzles are used, dispersal may be aided in part by pressurized ejection from nozzles. Dispersal mechanisms may similarly include an ultrasonic nebulizer, an air-blowing component such as a fan, impeller, pump, or micropump, which causes airflow past scent-diffusing material, carrying it and resulting aromas to user's nose or speeding up diffusion to accomplish the same. Automatically activated scent diffuser 108 may be incorporated in a home heating, ventilation, and/or air-conditioning system, permitting air circulation of such a system to aid in dispersal or diffusion of scent molecules. In an embodiment, where automatically activated scent diffuser 108 includes a heater, the heater may cause air currents through convection, which may have a similar effect to air blowing component. One or more dispersal mechanisms may include additional or alternative components, such as a wick, which may draw scent-diffusing material using capillary action from a container or enclosure to exposure to open air, where evaporation may disperse scent-diffusing material or enclosure to exposure to open air, where evaporation may disperse scent-diffusing material. A dispersal mechanism may include an ultrasonic nebulizer atomizing the scent-diffusing material and dispersing it to open air. Automatically activated scent diffuser may be configured to stop diffusing scent upon reception of a deactivation signal.

Figure 2A:
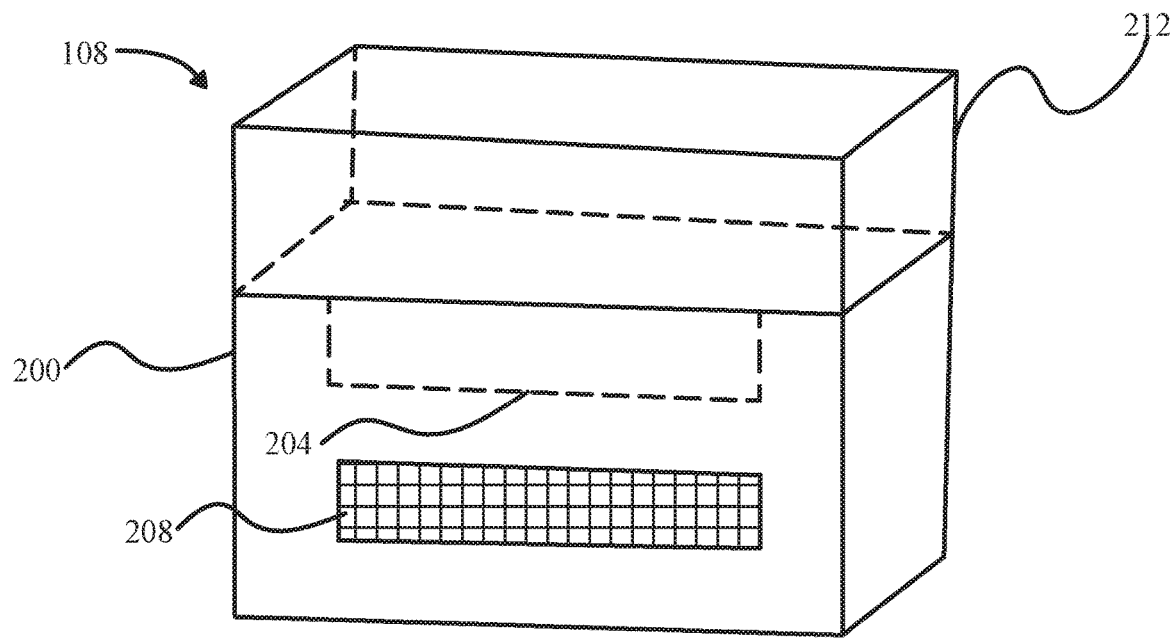
FIG. 2A is a schematic diagram illustrating a perspective view of an exemplary embodiment of an automatically activated scent diffuser.
Figure 2B:
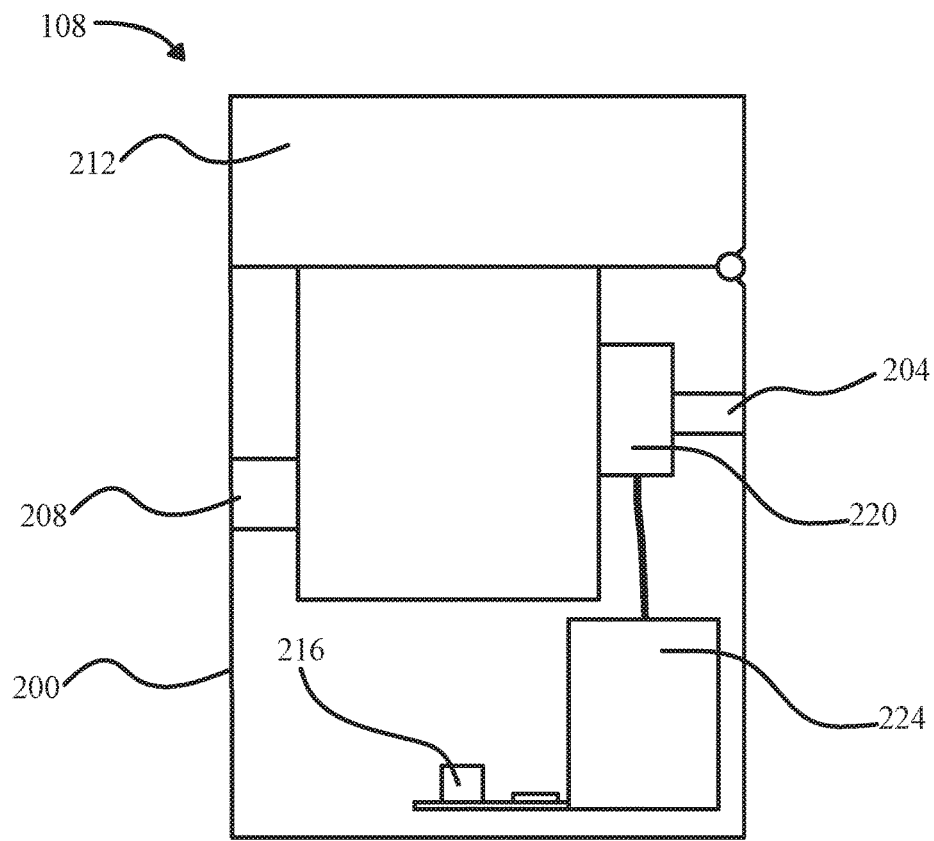
FIG. 2B is a schematic diagram illustrating a cutaway side view of an exemplary embodiment of an automatically activated scent diffuser.

Referring now to FIG. 2A, an exemplary embodiment of an automatically activated scent diffuser 108 is illustrated. Automatically activated scent diffuser 108 may have a housing 200, which may be in any suitable form, including without limitation a box form. Housing 200 may include an air intake 204, which may include or communicate with an aperture or selectively closable aperture of a compartment containing scent-diffusing material as described above. Housing 200 may include a diffusing vent 208, which may include a grid or other covering; diffusing vent 208 may include or communicate with an aperture or selectively closable aperture of a compartment containing scent-diffusing material as described above. Housing 200 may include a manually activated opening 212, such as a hinged and/or latched lid, which may be used to open housing 200 and/or compartment containing scent-diffusing material; manually activated opening 212 may cause scent release when opened, be used to insert additional scent-diffusing material in automatically activated scent diffuser 108, or the like. Referring now to FIG. 2B, housing 200 may contain one or more components of automatically activated scent diffuser 108 as described above, including a transceiver 216, such as a transceiver as described above, an electronic fan controller, an electric fan 220 with a motor, a battery 224, and the like. Housing 200 may include a receptacle for a scent wafer. Housing 200 may include a power switch.

Still referring to FIG. 2B, in operation, automatically activated scent diffuser 108 may prevent scent diffusion until receipt of an activation signal; for instance, where present, diffusing vent 208 and air intake 204 may be sealed initially, preventing scent dispersal. Upon an electronic activation signal, which may be received via any suitable means, including a signal to transceiver, automatically activated scent diffuser 108 may diffuse scent using any mechanisms, components, or combination thereof; for instance, and without limitation, where automatically activated scent diffuser 108 is as depicted in FIG. 2, an aperture at diffusing vent 208 and/or air intake 204 may be opened and fan may be activated, causing airflow from air intake 204 to diffusing vent 208 to carry scent molecules out into the air, so that user may smell them. In an alternative or additional embodiment, automatically activated scent diffuser 108 may include a scent-diffusing module attached to or incorporated in a mobile device such as without limitation a smart phone.

Referring again to FIG. 1, system 100 includes a control circuit 112. Control circuit 112 may include any electronic circuit that may be configured as described below; for instance, control circuit 112 may include a logic circuit incorporating one or more logic gates. Control circuit 112 may include a microprocessor, microcontroller, or any computing device as described below in reference to FIG. 5. As a non-limiting example, control circuit 112 may include a mobile computing device such as a "smartphone" or the like. Control circuit 112 may be communicatively connected to automatically activated scent diffuser 108 and/or at least a physiological sensor 104, where "communicative connection" is defined as a relationship between two or more devices or components whereby the two or more devices or components are capable of sending and/or receiving electrical or wireless signals to and/or from each other; for instance, where automatically activated scent diffuser 108 includes a transceiver or other wireless communication device, control circuit 112 may include a transceiver or other wireless communication device capable of communication with the transceiver or other wireless communication device of the automatically activated scent diffuser 108. Alternatively or additionally, control circuit 112 may be connected to automatically activated scent diffuser 108 and/or other components via a wired connection, by way of one or more intermediate devices, or by incorporation in the same component, chip, or circuit as automatically activated scent diffuser 108. Control circuit 112 may be configured to perform any methods or method steps as disclosed herein in any combination, including without limitation method 400 as described in further detail below. As a non-limiting example, control circuit 112 may be configured to receive a detection signal from the at least a physiological sensor 104, determine that the user is entering a pain-free state, and transmit the electronic activation signal to the automatically activated scent diffuser 108, as described in further detail below.

Figure 3:
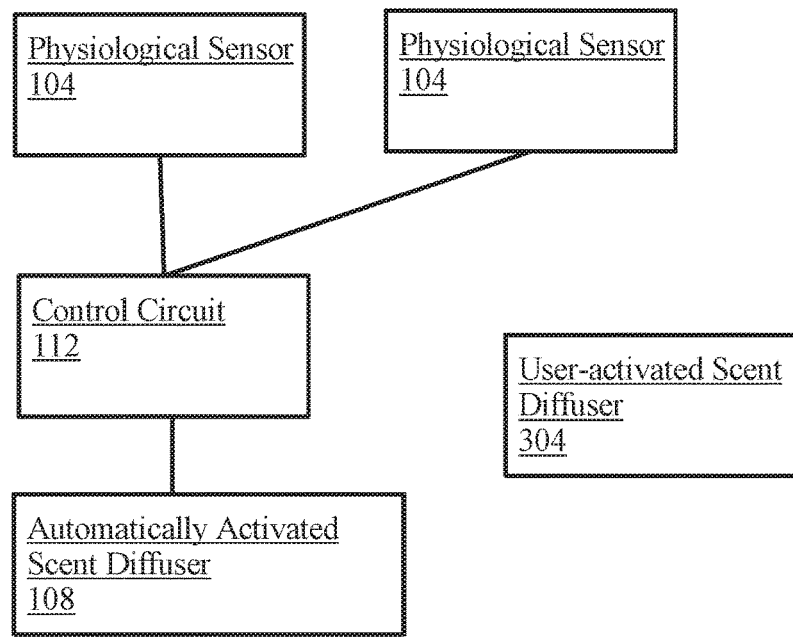
FIG. 3 is a block diagram illustrating an exemplary embodiment of a Pavlovian induction kit for inducing a Pavlovian association of a scent with a state of less-than-moderate pain.

Referring now to FIG. 3, an exemplary embodiment of a Pavlovian pain-free kit 300 is illustrated. In an embodiment, kit 300 includes at least a physiological sensor 104 configured to detect at least a physiological parameter of a user and transmit a detection signal; this may be implemented using any components, devices, or processes described above in reference to FIG. 1. Kit 300 includes an automatically activated scent diffuser 108 configured to receive an electronic activation signal and diffuse a scent as a function of the electronic activation signal; this may be implemented using any components, devices, or processes described above in reference to FIG. 1. Kit 300 includes a control circuit 112 configured to receive the detection signal from the at least a physiological sensor 104, determine that the user is entering a pain-free state, and transmit the electronic activation signal to the automatically activated scent diffuser 108. Control circuit 112 may be implemented and/or configured using any components, devices, or processes described above in reference to FIG. 1.

Still referring to FIG. 3, kit 300 includes a user-activated scent diffuser 304 that diffuses the scent upon activation by a user. User-activated scent diffuser 304 may include a scent diffuser that diffuses scent upon activation by user; activation by user, as used herein, means direct activation by a voluntary act on the part of the user, in a process that does not include sensing physiological parameters or determining a user state. For instance, user-activated scent diffuser 304 may include a switch that user turns on, causing release of scent, a manually activated opening 212, such as without limitation manually activated opening 212 depicted in FIG. 2, which exposes scent-diffusing material, a heat source such as a candle or an electric heater that user can apply to substance containing scent-diffusing material, a vibration generating component to generate ultrasonic vibrations, or the like. User-activated scent diffuser 304 may include a container, such as a portable container, that user may open and/or close manually; container may be constructed of any suitable material, including plastic, paper, metal, wood, or the like. Container may have a form of a box or wrapper that user opens to release scent. In a non-limiting example, user-activated scent diffuser 304 may include a container such as a box, wrapper, or sealed packet containing a scent wafer as described above, which user may activate by opening the container, and may deactivate by shutting or sealing the container. User-activated scent diffuser 304 may include any mechanism for scent diffusion and/or dispersal described above for automatically activated scent diffuser 108. User-activated scent diffuser 304 may be a separate device from automatically activated scent diffuser; alternatively, automatically activated scent diffuser 108 may function as user-activated scent diffuser by incorporation of one or more controls or features enabling user to activate scent diffusion. Scent diffused by user-activated scent diffuser 304 may be identical, or substantially identical, to scent diffused by automatically activated scent diffuser 108. User-activated scent diffuser 304 may include a scent-diffusing module attached to or incorporated in a mobile device such as without limitation a smart phone.

Figure 4:
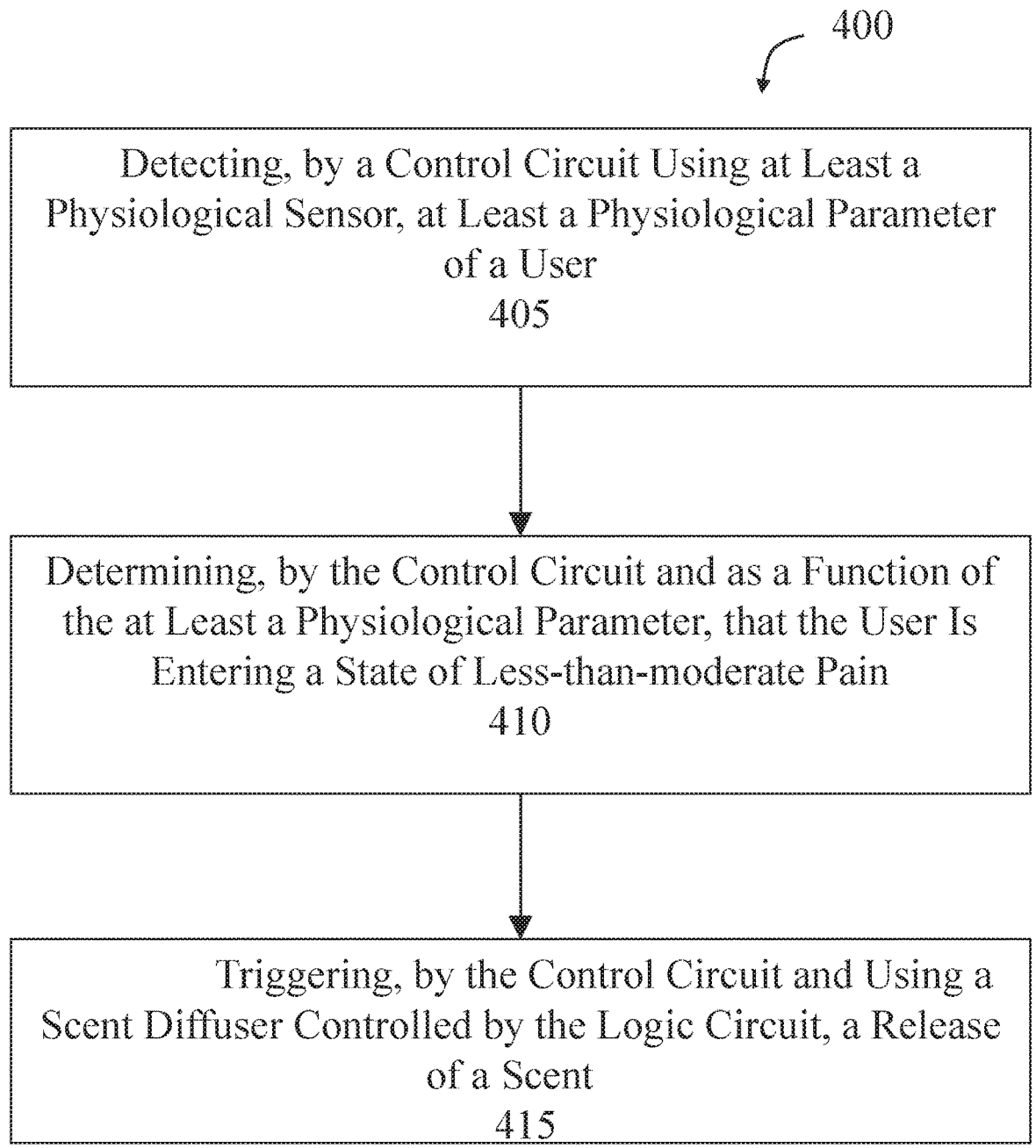
FIG. 4 is a flow diagram illustrating an exemplary embodiment of a method of inducing a Pavlovian association of a scent with a state of less-than-moderate pain.

Referring now to FIG. 4, an exemplary embodiment of a method 400 of inducing a Pavlovian association of a scent with a pain-free state is illustrated. At step 405, control circuit 112 detects, using at least a physiological sensor 104, at least a physiological parameter of a user. At least a physiological parameter of a user may include any of the physiological parameters as described above in reference to FIG. 1. Detection of at least a physiological parameter may include any of the processes, steps, and/or components, in any combination as described above in reference to FIG. 1. For example, at least a physiological sensor 104 may include an EKG designed to detect heart rate variability in a user. Heart rate may be detected by placing sensors such as electrodes onto the chest of a user which then detect the heart rate and/or electrical activity of the heart of a user. In an embodiment, detection of at least a physiological parameter of a user may be performed by a wearable device that is able to detect at least a physiological parameter of a user. For example, a user may wear on user's wrist an APPLE WATCH, series 4 or series 5, as produced by Apple of Cupertino, Calif. which contains electrodes and is able to perform an EKG of user's heart's electrical activity. In an embodiment, at least a physiological sensor 104 may include infrared sensor designed to detect temperature of a user. Temperature may be detected by infrared sensor placed on a user's forehead.

With continued reference to FIG. 4, at step 410, control circuit 112 ascertains, as a function of the at least a physiological parameter, that the user is entering a state of less-than-moderate pain. As used herein, that is a state in which a user experiences no pain, to very mild pain that does not interfere with activities of daily living. A state of less-than-moderate pain may be reflected as a score in the range 0-3 on the numeric rating scale for pain (NRS-11, as described above). The numeric rating scale is an 11-point scale for patient self-reporting of pain, used by adults and children 10 years old or older. Generally, a score of 0 indicates no pain; a score of 1-3 indicates very mild pain that does not interfere with activities of daily living; a score of 4-6 indicates moderate pain that interferes significantly with activities of daily living; and a score of 7-10 indicates severe pain that is disabling so that an individual is unable to perform activities of daily living. Activities of daily living may include a user's daily self-care activities. Self-care activities may include tasks such as bathing and showering, personal hygiene and grooming, such as brushing and combing one's hair, dressing, toilet hygiene such as going to the toilet, cleaning oneself, and getting back up, as well as functional mobility including one's ability to walk, get in and out of bed, get in and out of a chair, and one's ability to feed one's self. A state of less-than-moderate pain may include a state that is achieved in combination with the use of non-narcotic analgesics such as, for example, ibuprofen, other non-steroidal anti-inflammatory drugs ("NSAIDs") such as ketorolac and/or diclofenac, and/or acetaminophen.

With continued reference to FIG. 4, detection of transition into a state of less-than-moderate pain may include detection of a physiological parameter correlated with entry into a pain state. For example, correlations have been noted of a positive galvanic skin response (GSR) such as increased sweating and increased heart rate and blood pressure as pain intensity increases, as well as respiratory rates outside of normal limits as pain intensity increases. In an embodiment, where a physiological parameter is correlated with an occurrence of a high pain-state, determination of absence of a physiological parameter may indicate entry into a state of less-than-moderate pain. For example, where a positive galvanic skin response is noted, such as increased heart rate above 100 beats per minute, and/or reduced or shallow breathing less than 12 breaths per minute or elevated breaths of more than 20 breaths per minute which all may be indicative of a patient experiencing pain, absence of such physiological parameters may be indicative of a patient not experiencing moderate or severe pain. For example, a patient who is not experiencing pain may not have a positive galvanic skin response, may have a normal resting heart rate between 60 to 100 beats per minute and may have a normal respiratory rate between 12 to 20 breaths per minute. In yet another non-limiting example, a patient who is experiencing pain may have blood pressure readings outside of normal limits such as high blood pressure reflected in blood pressure measurements between 140-200 mm Hg systolic over 80-100 mm Hg diastolic, and/or low blood pressure such as when a patient is in septic shock reflected in blood pressure measurements between 70-90 mm Hg systolic over 40-60 mm Hg diastolic. A user not experiencing moderate or severe pain may have normal blood pressure readings ranging between 90-120 mm Hg systolic over 60-80 mm Hg diastolic.

With continued reference to FIG. 4, detection of entry into a pain-free state may include comparing a physiological parameter during a pain state to a physiological parameter during a pain free state. In an embodiment, a physiological parameter such as heart rate may be detected while user is experiencing a known pain-state, such as for example immediately following major surgery in post-op recovery, and/or immediately after being brought into the hospital following a major car accident and/or machine accident with visibly injury. At a second time subsequent to the first time a second physiological parameter, which may be the same physiological parameter and/or a different physiological parameter, may be detected during a pain-free state. For example, several days after surgery when a user is recovering at home, heart rate may again be detected. Heart rate measured while at home may then be compared to heart rate measured immediately following surgery where differences in heart rate may reflect entry into a pain-free state and/or greater degree of relaxation and comfort of a user. For example, an elevated heart rate experienced after surgery in post-op may be compared to a lower more normal heart rate experienced days later while a patient recovers at home, thereby indicating entry into a pain-free state. In yet another non-limiting example, a first physiologic response such as blood pressure may be detected in a user immediately after suffering an accident in the intensive care unit. At a second time, subsequent to the first time, a second physiological parameter such as heart rate may be detected the next day when the user is transferred to a general unit floor for observation. High blood pressure noted immediately after an accident as compared to a heart rate within normal limits the next day on the general unit floor may indicate a greater state of relaxation and that user has transitioned to a state of less-than-moderate pain. In an embodiment, determination that a user is entering a pain-free state may be augmented by a user response. For example, in an embodiment where changes in physiological parameters between pain state and pain free state are not pronounced, and/or are hard to decipher, user may override control circuit 112 such as for example by pressing a button located on control circuit that informs control circuit 112 that user is entering a pain-free state. This may be similar to a patient-controlled analgesia (PCA) which a user may activate for pain relief by pressing a button which triggers pain medication to be delivered to the user. In this instance, when user experiences a pain-free state, user may indicate to control circuit 112 that user is entering a pain-free state and as such a release of a scent may be triggered, as described in more detail below.

With continued reference to FIG. 4 at step 415 control circuit 112 triggers a release of a scent; this may be performed using automatically activated scent diffuser 108, using any component, process step, or combination thereof described above in reference to FIGS. 1-3. In an embodiment, scent is not released until triggering; for instance, automatically activated scent diffuser 108 may allow no scent, or substantially no scent, to be released and/or detected except upon receipt of electronic activation signal. In an embodiment, this may ensure that user establishes a Pavlovian correlation between scent and pain state; where user is exposed to scent only upon entry into pain free state, user may develop a strong Pavlovian association between scent and the act of a pain-free state. This may ensure that future exposure to scent will cause user to experience a pain-free state more quickly. In an embodiment, control circuit may detect that user has entered a pain-free state and deactivate automatically activated scent diffuser 108. Alternatively or additionally, control circuit 112 may determine that a time limit has passed and deactivate the automatically activated scent diffuser 108 as a function of the determination. Time limit may be calculated from any suitable event. Deactivation may, in an embodiment, prevent Pavlovian association of the smell with waking or other events besides a pain-free state.

In operation, and still viewing FIG. 4, method 400 may involve a first period in which steps 405-415 are followed iteratively; for instance, system 100 may be used on a daily basis post operation for a number of days, sometimes possibly even several times per day to administer scent to user at entry into a pain-free state, creating an association, via classical conditioning, between the scent and the moment of entry into a pain-free state. User may then employ kit 300 to aid in pain management; for instance, user may take user-activated scent diffuser 304 after discharge from a hospital and/or surgical center, at a moment user experiences pain, may position user-activated scent diffuser 304 near user and activate scent diffusion. Pavlovian association between scent and pain response may cause user to decrease dependency on pain medications and thus offer a medication free way to manage pain. Further, Pavlovian association between scent and pain may be used successfully in patients needing pain medication in combination, to assist in successful weaning off of opiates and assist in transition of care. System 100 may be utilized in combination with a non-narcotic analgesic such as for example, ibuprofen, other non-steroidal anti-inflammatory drugs such as ketorolac and/or diclofenac, and/or acetaminophen. In an embodiment, system 100 may aid in amplifying a user's response to a non-narcotic analgesic to induce a pain-free or pain reduced state, without the need for stronger medications such as opiates, narcotics, and other controlled substances which can lead to addiction and misuse. This could be of substantial impact as drug overdose is the leading cause of accidental death in the United States. Kit 300 may advantageously allow user to begin the Pavlovian response in the hospital immediately after admission such as for surgery, an accident, and/or treatment, and continue as user is discharged and care is continued in user's home. User-activated scent diffuser 304 may require no electricity in an embodiment; as a result, user may be able to carry and use it in situations where electrical power is limited or not present, such as on camping trips or during emergencies or extreme weather events. In addition, the user-activated scent diffuser 304 may enable the user to avoid carrying additional electrical cords, connectors, chargers and electrical plugs including those necessary for use with different international voltages. User-activated scent diffuser 304 may similarly be used in circumstances where electronic devices and/or wireless communication may be restricted, such as airplanes or hospital rooms.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A "machine-readable" medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 5:
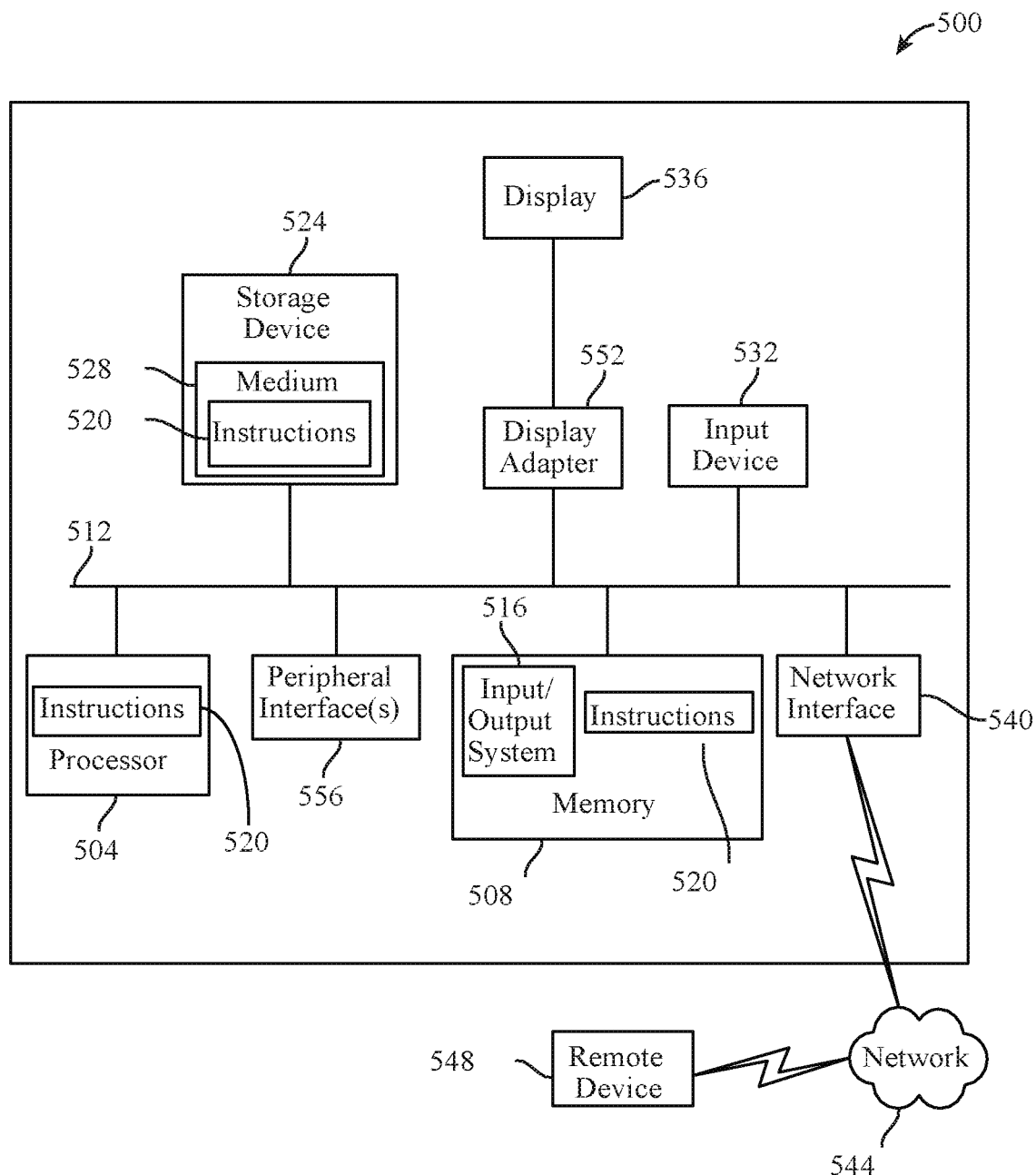
FIG. 5 is a block diagram of a computing system that can be used to implement any of the methodologies disclosed herein, and any one or more portions thereof.

FIG. 5 shows a diagrammatic representation of one embodiment of a computing device in the exemplary form of a computer system 500 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 500 includes a processor 504 and a memory 508 that communicate with each other, and with other components, via a bus 512. Bus 512 may include any of several types of bus structures including, but not limited to, a memory bus, a memory controller, a peripheral bus, a local bus, and any combinations thereof, using any of a variety of bus architectures.

Memory 508 may include various components (e.g., machine-readable media) including, but not limited to, a random-access memory component, a read only component, and any combinations thereof. In one example, a basic input/output system 516 (BIOS), including basic routines that help to transfer information between elements within computer system 500, such as during start-up, may be stored in memory 508. Memory 508 may also include (e.g., stored on one or more machine-readable media) instructions (e.g., software) 520 embodying any one or more of the aspects and/or methodologies of the present disclosure. In another example, memory 508 may further include any number of program modules including, but not limited to, an operating system, one or more application programs, other program modules, program data, and any combinations thereof.

Computer system 500 may also include a storage device 524. Examples of a storage device (e.g., storage device 524) include, but are not limited to, a hard disk drive, a magnetic disk drive, an optical disc drive in combination with an optical medium, a solid-state memory device, and any combinations thereof. Storage device 524 may be connected to bus 512 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 524 (or one or more components thereof) may be removably interfaced with computer system 500 (e.g., via an external port connector (not shown)). Particularly, storage device 524 and an associated machine-readable medium 528 may provide nonvolatile and/or volatile storage of machine-readable instructions, data structures, program modules, and/or other data for computer system 500. In one example, software 520 may reside, completely or partially, within machine-readable medium 528. In another example, software 520 may reside, completely or partially, within processor !!04.

Computer system 500 may also include an input device 532. In one example, a user of computer system 500 may enter commands and/or other information into computer system 500 via input device 532. Examples of an input device 532 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 532 may be interfaced to bus 512 via any of a variety of interfaces (not shown) including, but not limited to, a serial interface, a parallel interface, a game port, a USB interface, a FIREWIRE interface, a direct interface to bus 512, and any combinations thereof. Input device 532 may include a touch screen interface that may be a part of or separate from display 536, discussed further below. Input device 532 may be utilized as a user selection device for selecting one or more graphical representations in a graphical interface as described above.

A user may also input commands and/or other information to computer system 500 via storage device 524 (e.g., a removable disk drive, a flash drive, etc.) and/or network interface device 540. A network interface device, such as network interface device 540, may be utilized for connecting computer system 500 to one or more of a variety of networks, such as network 544, and one or more remote devices 548 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 544, may employ a wired and/or a wireless mode of communication. In general, any network topology may be used. Information (e.g., data, software 520, etc.) may be communicated to and/or from computer system 500 via network interface device 540.

Computer system 500 may further include a video display adapter 552 for communicating a displayable image to a display device, such as display device 536. Examples of a display device include, but are not limited to, a liquid crystal display (LCD), a cathode ray tube (CRT), a plasma display, a light emitting diode (LED) display, and any combinations thereof. Display adapter 552 and display device 536 may be utilized in combination with processor 504 to provide graphical representations of aspects of the present disclosure. In addition to a display device, computer system 500 may include one or more other peripheral output devices including, but not limited to, an audio speaker, a printer, and any combinations thereof. Such peripheral output devices may be connected to bus 512 via a peripheral interface 556. Examples of a peripheral interface include, but are not limited to, a serial port, a USB connection, a FIREWIRE connection, a parallel connection, and any combinations thereof.

Figure 6:
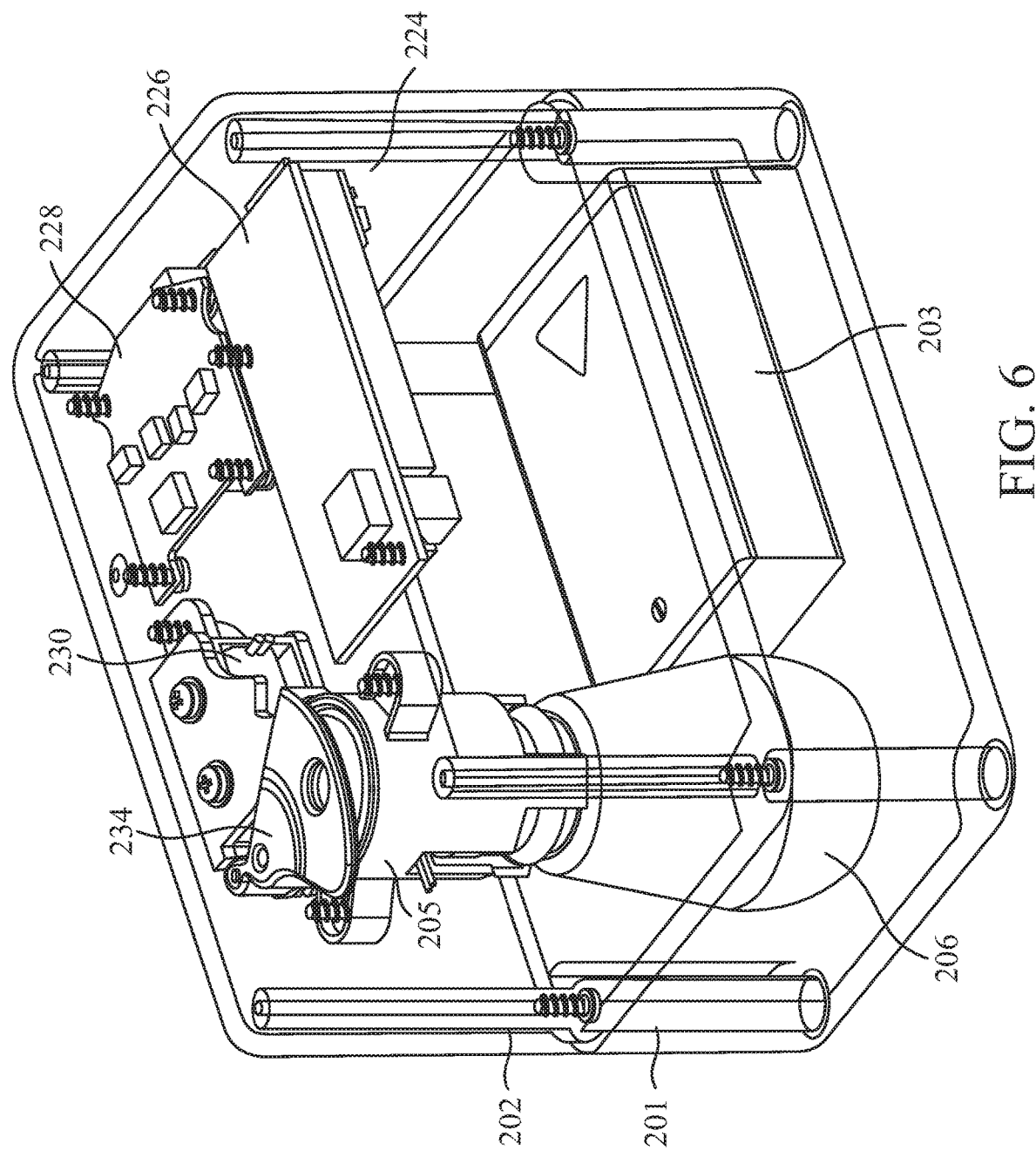
FIG. 6 is a perspective view of an exemplary embodiment of an automatically activated scent diffuser.

FIG. 6 illustrates another embodiment of the automatically activated scent diffuser 108. The system preferably comprise s a generally rectangular lower housing portion 201 which includes a compartment 203 for standard alkaline batteries such as size AA batteries, or a rechargeable equivalent, and an upper housing portion 202 which encloses circuitry and a mounting collar or bottle holder 205 for receiving a generally cylindrical bottle 206 adapted to contain a fragrance fluid. Preferably, a lower peripheral rim 222 of the upper housing portion 202 mates with an upper peripheral rim 221 of the lower housing portion 201, and the two housing portions are secured together by screws, threaded through horizontal flanges 209 formed at respective corners of the peripheral rims. It will be apparent that alternative securing structures can be substituted for the screws, by those having ordinary skill in the art.

The circuitry mounted in the upper housing portion 202 suitably comprises a voltage regulator 224 (e.g. model D24V10F5 available from Pololu Corp of Las Vegas Nev., USA), a communications module, for example a BLUETOOTH transceiver 226 (such as SparkFun model nRF52832, available from SparkFun Electronics of Niwot, Colo., USA), an ultrasonic transducer PCB (printed circuit board) 228, a solenoid or linear actuator 230, and a solenoid control circuit 232 (available from Efcom of Rehovot, Israel). As in the case of ultrasonic transducers used in home humidifiers, PCB 228 drives a generally annular ultrasonic transducer arranged at an outlet opening of the bottle 205 of fragrance fluid; the transducer serves to nebulize the fluid, in order to emit the fragrance into the ambient air surrounding the user of the diffuser. Also mounted in upper housing portion 202 is the bottle holder 205 for receiving the bottle 206 of fragrance fluid. On top of the bottle holder, there is pivotably secured a horizontally oriented shutter 234, formed with a vertical bore or hole 236. Horizontally oriented shutter 234 is mounted at a corner thereof for rotation on a vertically aligned solenoid pin 237, so that shutter 234 can be rotated, for example about 90 degrees, alternately in a first rotation direction and in a second rotation direction. The solenoid 230 is mechanically coupled to the shutter 234, so that the shutter serves as a valve, opening the bottle when the hole 236 in the shutter is aligned with a central opening 246 at the top of the bottle, and closing the bottle when the hole 236 has been pivoted sideways, out of alignment with the bottle central opening 246. Alternatively, the shutter can be pivoted by an electric servo-motor (such as model F S90, available from FeeTech RC Model Co. Ltd. of Shenzhen, China).

Figure 7:
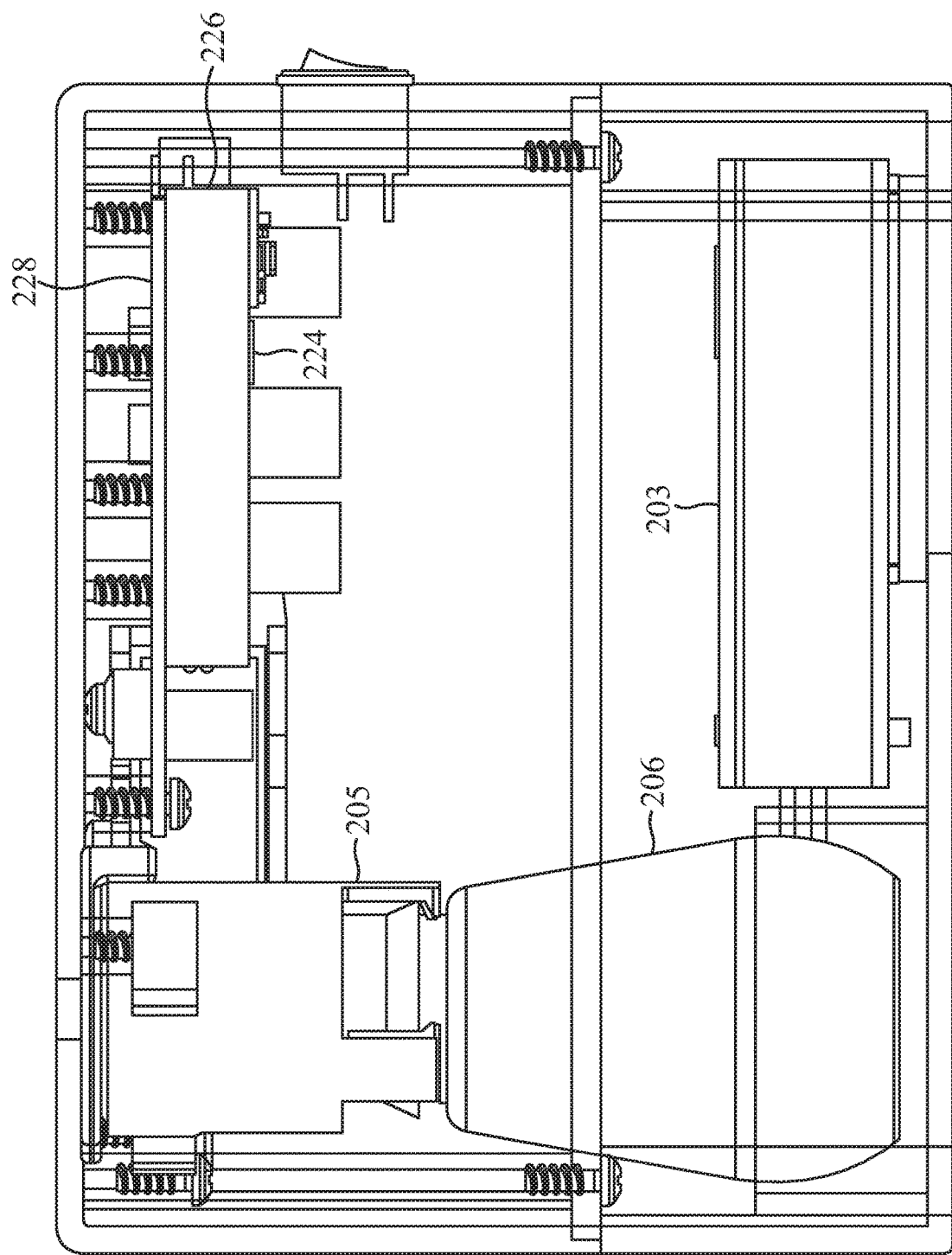
FIG. 7 is a side view, partly in cross section, of the diffuser of FIG. 6.

FIG. 7 is a side view of the diffuser, showing the housing port ions in phantom, in order to show an exemplary configuration of the bottle 205, the bottle holder 206 and the respective circuit boards.

Figure 8B:
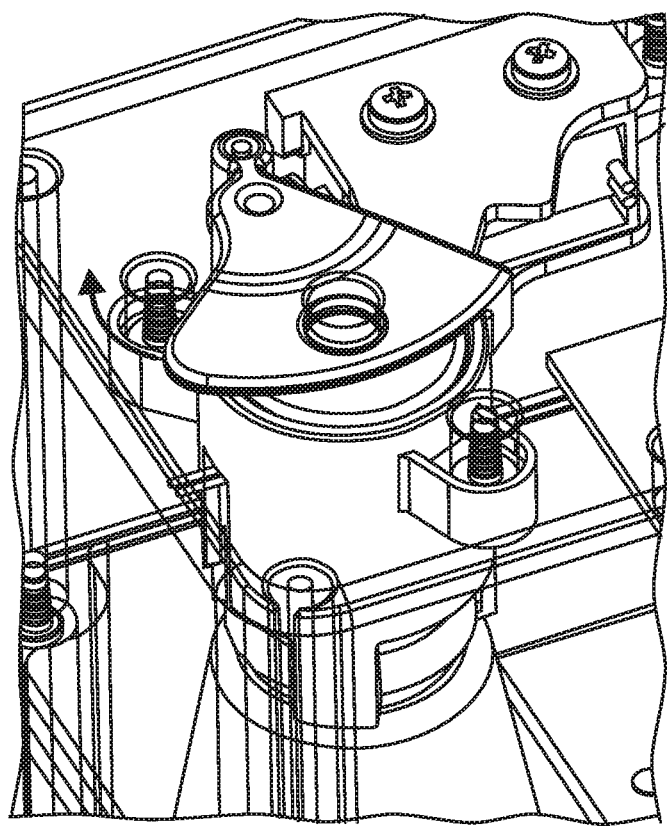
FIGS. 8A & 8B illustrate a bottle-open configuration of the diffuser of FIG. 6.
Figure 8A:
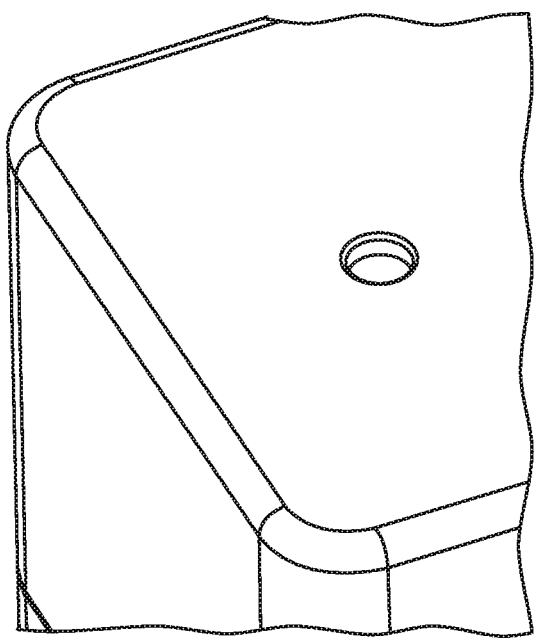
Figure 9B:
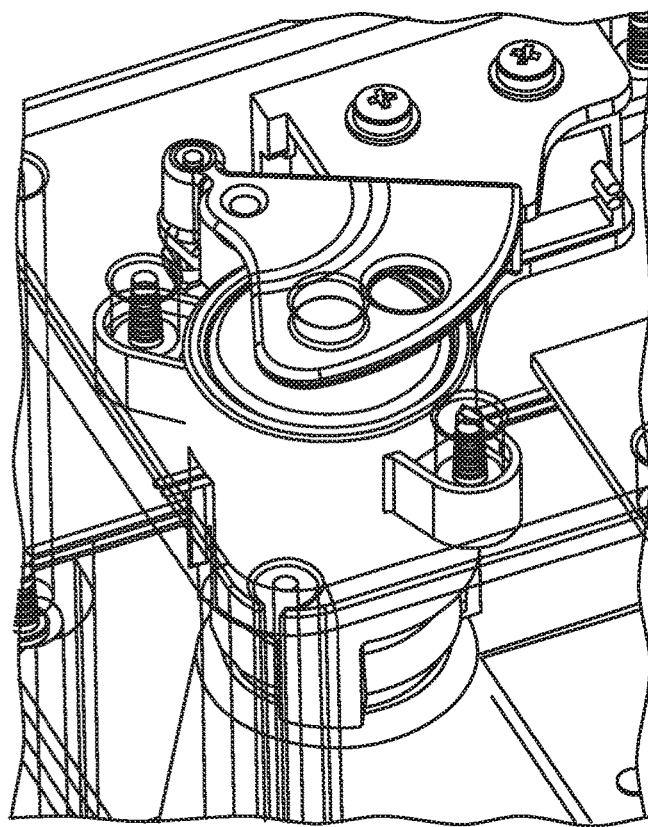
FIGS. 9A & 9B illustrate a bottle-closed configuration of the diffuser of FIG. 6.
Figure 9A:
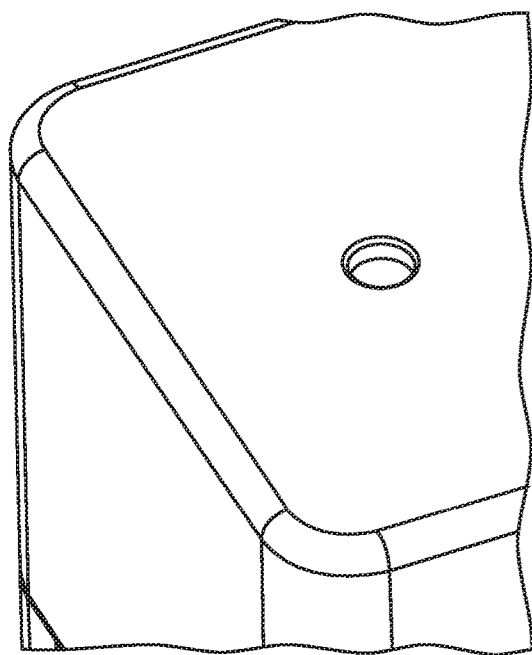

FIGS. 8A and 8B show, respectively, the diffuser exterior and the diffuser interior when the shutter 234 is aligned to open the bottle 205. FIGS. 9A and 9B show, respectively, the diffuser exterior and diffuser interior when shutter 234 is aligned to close bottle 205 by presenting a solid portion of shutter 234 to the central opening 246 of bottle 205. For example, as shown in FIG. 8B, shutter 234 can have a generally triangular shape with a pivot point at one vertex, subtending an angle of 60 degrees. Hole 236 can be formed near an edge of the triangle, remote from the pivot point. Rotating shutter 234 by 20 degrees or so, for example counterclockwise (viewed from above as in FIG. 9B) brings hole 236 out of alignment with opening 246 of bottle 205, thereby bringing a solid portion of shutter 234 adjacent to opening 246 and closing bottle 205.

Figure 10A:
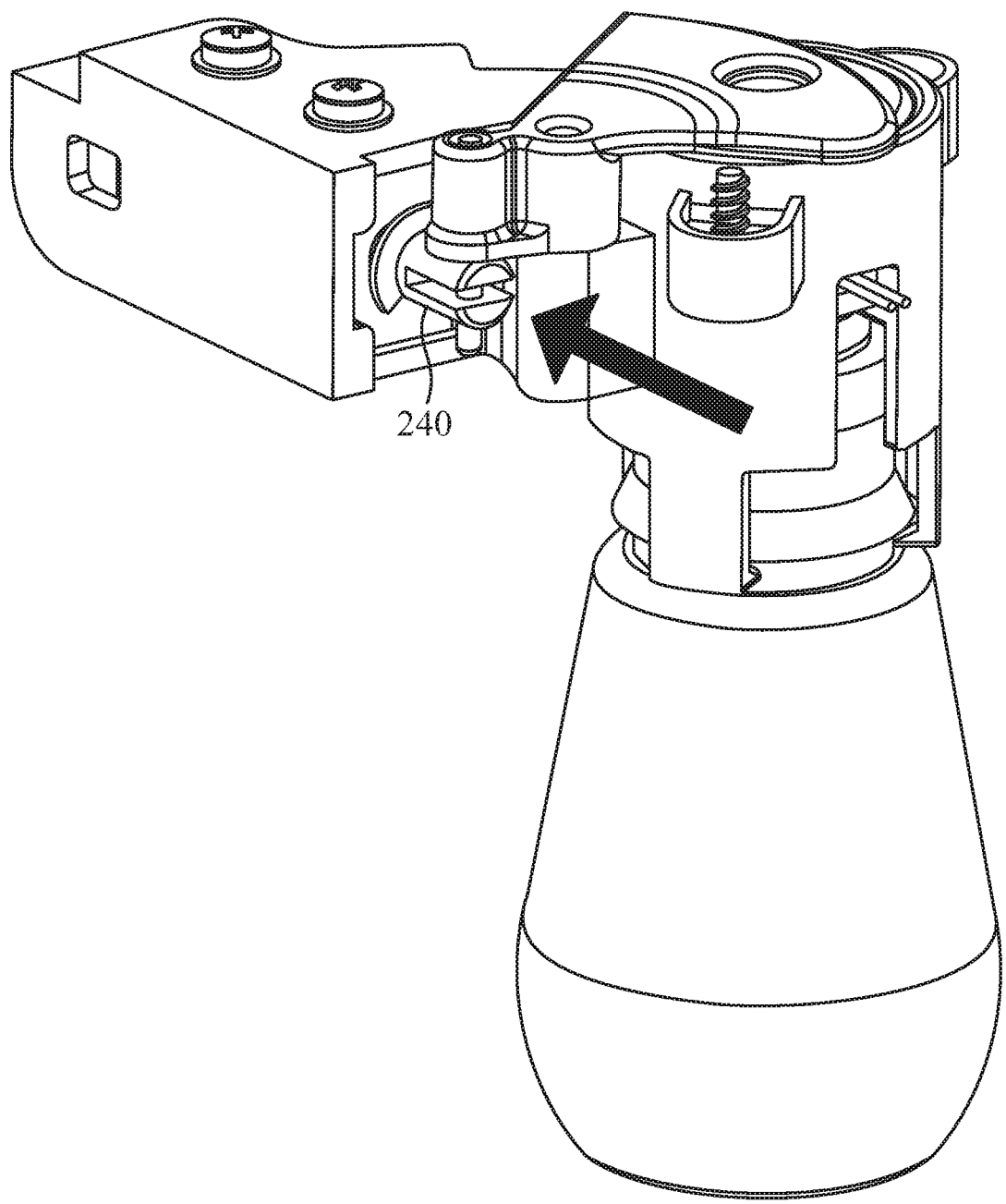
FIG. 10A illustrates a piston-retraction stroke or movement of a solenoid in the diffuser of FIG. 6.
Figure 10B:
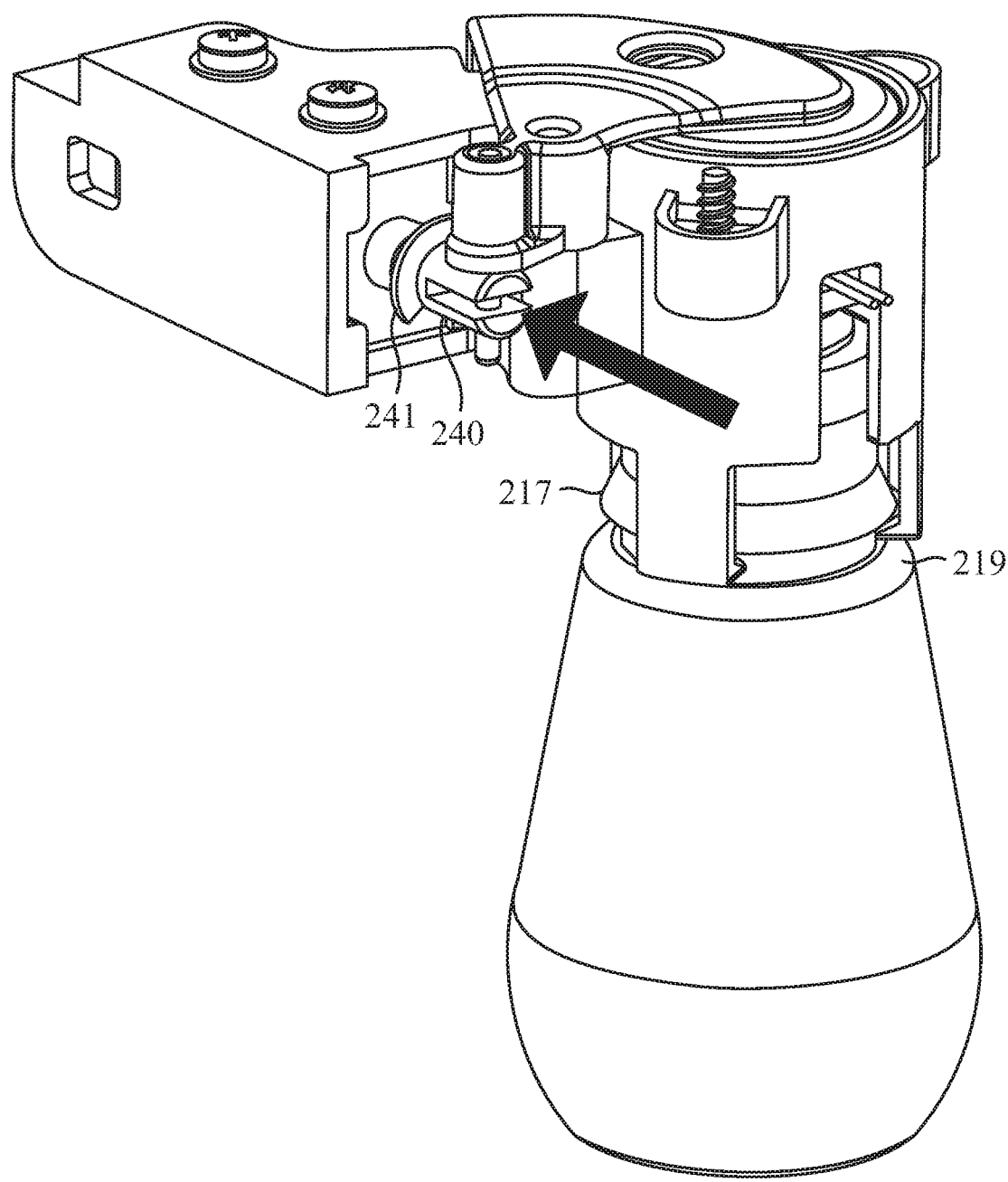
FIG. 10B illustrates a piston-extension stroke or movement of the solenoid.

FIG. 10A and FIG. 10B respectively show how solenoid 230 actuates shutter 234 to switch between a first, bottle-open, configuration and a second, bottle-closed, configuration. A coupling between solenoid 230 and shutter 234 includes a vertically aligned central pin 239 and a vertically aligned solenoid pi n 237. The pins are each received within a respective cylindrical sleeve, and the sleeves are rigidly connected to each other by a horizontal bridge 238. A lower end of solenoid pin 237 is received in a vertical bore formed in solenoid piston or plunger 240. Energizing the coil within solenoid 230 retracts piston 240, causing it to exert a pulling force as shown by the arrow in FIG. 10A. An annular stop 241 on the exterior of piston 240 limits the distance that the piston can travel, because stop 241 comes into abutment with an end face of solenoid 230, as may be seen by comparing FIG. 10B (extended) with FIG. 10A (retracted). Central pin 239 is fixed in a portion of bottle holder 205, so bridge 238 causes the sleeve around pin 239 to rotate, and shutter 234 rotates clockwise until shutter hole 236 is vertically aligned with bottle opening 246, allowing scented fluid to be released from the bottle. Conversely, when solenoid 230 is de-energized, piston 240 moves outwardly with respect to solenoid 230, as shown by the arrow in FIG. 10B, and bridge 238 transmits this motion to the sleeve surrounding central pin 239, causing shutter 234 to rotate counter-clockwise, thereby closing bottle 206 and stopping release of scented fluid. Bottle 206 is preferably somewhat tapered, larger in diameter near the bottom, and formed near its top with a radially projecting annular collar 217, beneath which is an annular groove or recess 219, to facilitate secure gripping by bottle holder 205.

Figure 11A:
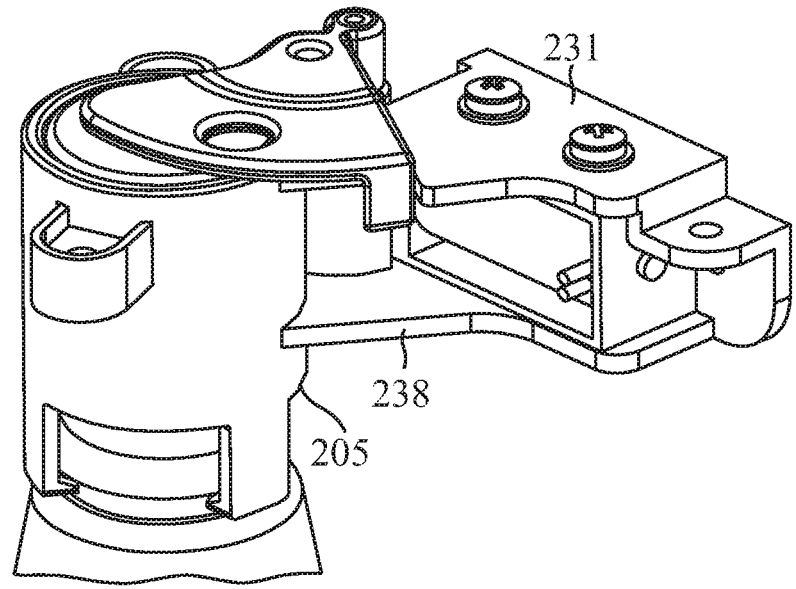
FIGS. 11A & 11B illustrate, from opposing directions, mechanical connections between the solenoid of FIGS. 10A & 10B, and a bottle holder portion of the diffuser of FIG. 6.
Figure 11B:
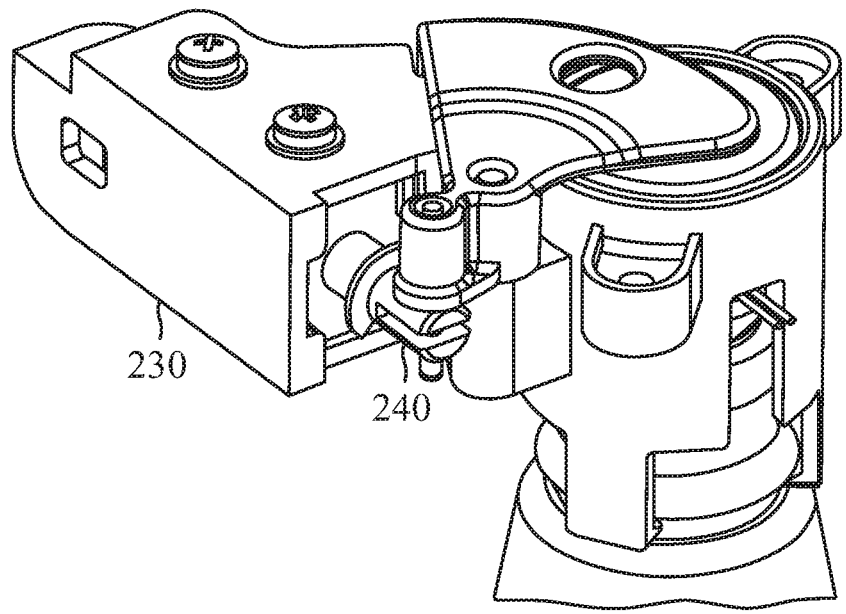

FIG. 11A is a slightly enlarged view similar to FIG. 10B, showing a flat vertical side face of solenoid 230, adapted for fastening to a vertical sidewall in the diffuser. FIG. 11B is a view of the same structure, rotated 180 degrees, to show mechanical connections between bottle holder 205 and solenoid 230.

Figure 12:
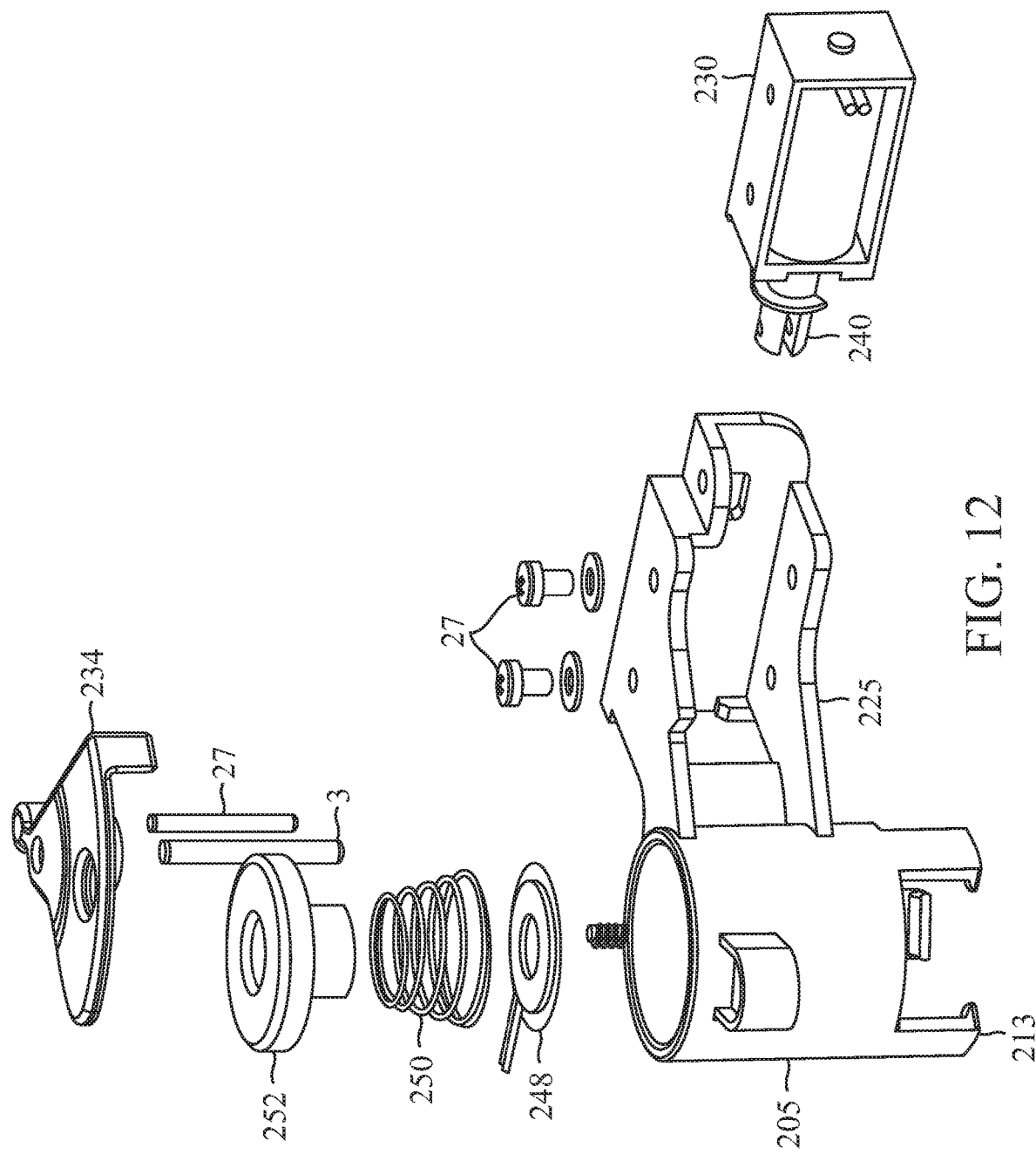
FIG. 12 is an exploded view, showing components of the bottle holder and solenoid portions of the diffuser of FIG. 6.

FIG. 12 is an exploded view, showing components which are assembled to couple bottle holder 205 and solenoid 230 together and to perform fragrance release functions. Bottle holder 205 is preferably a molded plastic element, forming a hollow vertical cylinder with a plurality of depending latches or claws 213 which in vertical cross-section are L-shaped, for example three claws spaced at 120-degree circumferential intervals. The claws point radially inward and are radially resilient, so that a bottle 206 can be inserted axially upwardly into holder 205, and the claws will bow outward momentarily, slide across collar 217 of the bottle, and snap-fit into annular groove 219, thereby holding bottle 206 securely, even if the entire diffuser structure is subsequently vibrated or moved from place to place. Since the bottle is replaceable, an institution such as a hospital can "swap out" or replace the bottle and use the same device with a subsequent patient. A new sterile scent bottle or source can be used for each new patient.

Holder 205 is preferably formed with a laterally projecting U-shaped channel 225 adapted to secure solenoid 230 within it. As shown, channel 225 preferably has a horizontal top wall, a horizontal bottom wall, and a connecting vertical sidewall which interconnects the top & bottom walls, at wall edges remote from the hollow cylindrical portion. Channel 225 is dimensioned to snugly receive solenoid 230 between its top & bottom walls, and against its sidewall. Preferably, respective holes are formed in the top wall and in a top wall of solenoid 230, so that a pair of screws 227 can be inserted through the top wall and into solenoid 230, to thereby secure solenoid 230 within channel 225.

In order to facilitate evaporation and dispersion of scented fluid from bottle 206, a generally disk-shaped ultrasonic transducer 248 is provided, dimensioned to be received within holder 205. Such ultrasonic transducers are widely used in residential humidifying devices, and suitable models are well known to those having ordinary skill in the air treatment and fragrance dispensing arts. As previously mentioned, the transducer is suitably driven by a transducer driving circuit board 228. Optionally, a fan can be provided to help disperse scent droplets produced by the ultrasonic transducer. A coil spring 250 is placed on top of transducer 248. A leading tube 252 with a top annular flange is place d on top of spring 250, so that spring 250 can urge leading tube 252 upward toward shutter 234. This tends to minimize leakage of volatile components of the fragrance fluid from bottle 206 at times when dispensing is not intended. As previously mentioned, a central pin 239 rides within a cylindrical sleeve which is secured to a bottom surface of shutter 234, and a solenoid pin 237 rides within another cylindrical sleeve connected by a bridge 238 to the central pin's sleeve.

Figure 13:
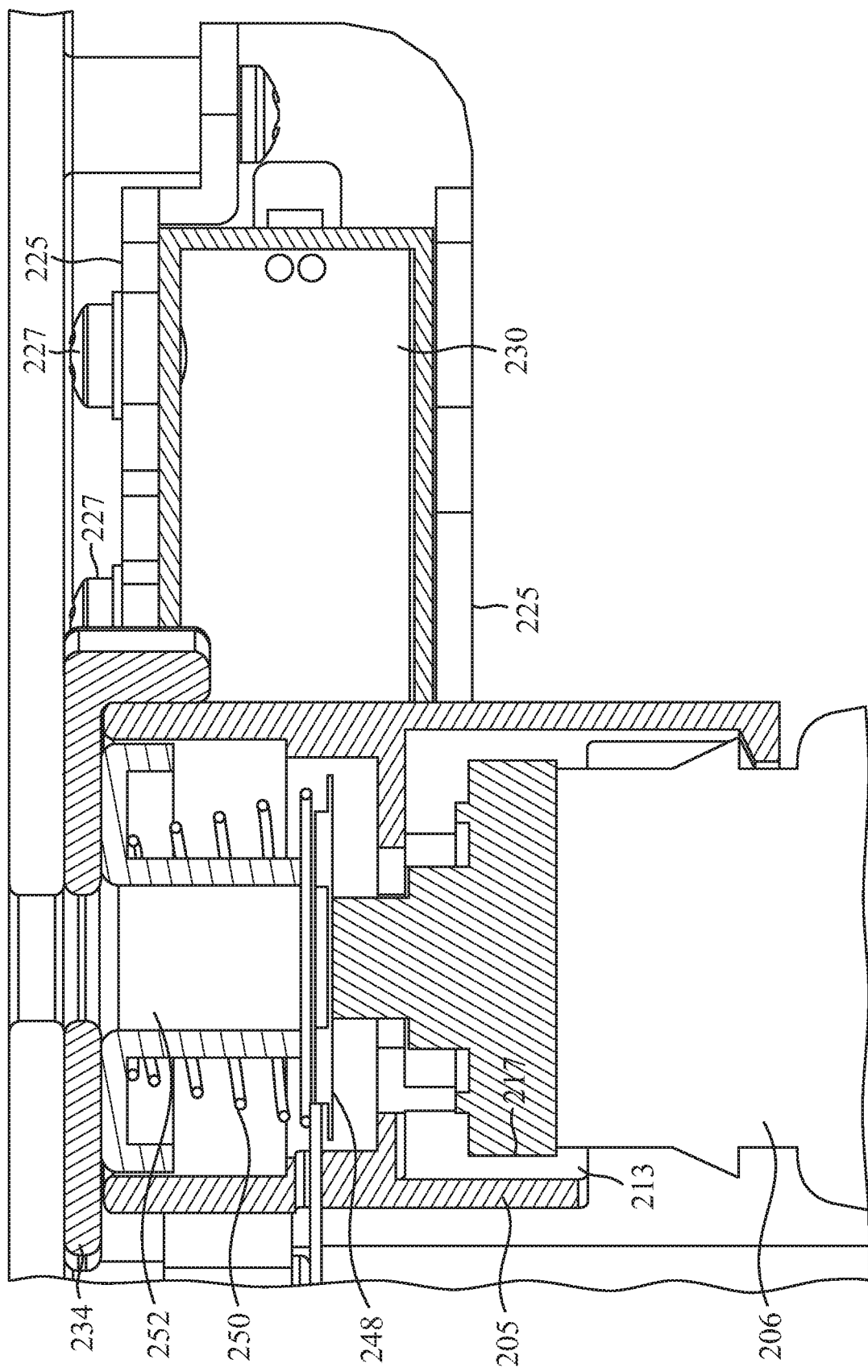
FIG. 13 is a schematic view, partly in cross section, showing an assembled state of the diffuser components of FIG. 12.

FIG. 13 is a view, partly in cross-section, showing the components of FIG. 12 in an assembled state, ready for operation.

The foregoing has been a detailed description of illustrative embodiments of the invention. Various modifications and additions can be made, without departing from the spirit and scope of this invention. Features of each of the various embodiments described above may be combined with features of other described embodiments, as appropriate, in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods and systems according to the present disclosure. Accordingly, this description is meant to be taken only by way of example, and not to otherwise limit the scope of this invention.

Exemplary embodiments have been disclosed above and illustrated in the accompanying drawings. It will be understood by those having ordinary skill in the art that various changes, omissions and additions may be made to that which is specifically disclosed herein, without departing from the spirit and scope of the present invention.

What is claimed is:

1. A method of inducing a Pavlovian association of a scent with a transition into a state of less-than-moderate pain, the method comprising:
   detecting, by a control circuit using at least a physiological sensor, at least one physiological parameter of a user;

ascertaining, in the control circuit and as a function of the at least one physiological parameter, that the user has transitioned into a state of less-than-moderate pain; and triggering, by the control circuit and using a scent diffuser controlled by the control circuit, release of a scent.

2. The method of claim 1, further comprising performing the steps of claim 1 iteratively during each of a series of transitions into a state of less-than-moderate pain, thereby conditioning said user, upon perception of said scent, to mentally associate said scent with relief from pain.

3. The method of claim 2, further comprising, after formation of said mental association, manually releasing said scent into ambient air near said user, to trigger an expectation of relief from pain.

4. The method of claim 1, wherein said step of ascertaining a transition comprises:

detecting a first parameter value, indicative of at least a moderate level of pain; and detecting a second parameter value, indicative of said state of less-than-moderate pain.

5. The method of claim 1, wherein the at least one physiological parameter comprises a heart rate variability pattern.

6. The method of claim 1, wherein ascertaining that the user is transitioning into a state of less-than-moderate pain further comprises first detecting a physiological parameter during a prior state of at least moderate pain.

7. The method of claim 1, wherein ascertaining that the user is transitioning into a state of less-than-moderate pain further comprises:

detecting a first physiological parameter value of the at least one physiological parameter at a first time during a state of at least moderate pain;

detecting a second physiological parameter value of the at least one physiological parameter at a second time during a state of less-than-moderate pain; and comparing the second physiological parameter value to the first physiological parameter value as a function of a current pain-state.

8. The method of claim 7 further comprising:

ascertaining, by the control circuit, that the user has entered a state of less-than-moderate pain; and deactivating the scent diffuser, as a function of the ascertainment.

9. The method of claim 7 further comprising:

determining, by the control circuit, that a time limit has passed; and deactivating the scent diffuser as a function of the determination.

10. The method of claim 1, further comprising:

accepting, in said control circuit, a level of pain value reported by said user; and combining said reported value with said at least one physiological parameter value.

11. The method of claim 1, further comprising containing said scent, until said triggering happens.

12. The method of claim 1 further comprising deactivating, by the control circuit, the scent diffuser.

13. A system for inducing a Pavlovian association of a scent with a state of less-than-moderate pain, the system comprising:

at least one physiological sensor arranged to sense at least a physiological parameter of the user, wherein the at least one physiological sensor is configured to detect the at least a physiological parameter of the user and to transmit a detection signal;

an automatically activated scent diffuser, wherein the automatically activated scent diffuser is configured to receive an electronic activation signal and to diffuse a scent as a function of the electronic activation signal; and a control circuit configured to receive the detection signal from the at least one physiological sensor, to ascertain that the user is entering a state of less-than-moderate pain, and to transmit the electronic activation signal to the automatically activated scent diffuser.

14. The system of claim 13, wherein the at least one physiological sensor includes at least an electrophysiologic sensor.

15. The system of claim 14, wherein the at least an electrophysiologic sensor includes an electrocardiogram.

16. The system of claim 14 wherein the at least an electrophysiologic sensor includes a heart rate monitor.

17. The system of claim 14, wherein the at least an electrophysiologic sensor includes an electroencephalogram.

18. The system of claim 13, wherein the at least one physiological sensor includes a body temperature sensor.

19. The system of claim 13, wherein the at least one physiological sensor includes a dolorimeter.

20. The system of claim 13, wherein the automatically activated scent diffuser includes an aperture with an electronically activated door.

21. The system of claim 13, wherein the control circuit is further configured to transmit, to the automatically activated scent diffuser, a deactivation signal.

22. A kit adapted to condition a user to perceive less pain, the kit comprising:

at least one physiological sensor, wherein the at least one physiological sensor is configured to detect at least a physiological parameter of a user, and to transmit a detection signal;

an automatically activated scent diffuser, wherein the automatically activated scent diffuser is configured to receive an electronic activation signal and to diffuse a scent in response to the electronic activation signal;

a control circuit configured to receive the detection signal from the at least one physiological sensor, to ascertain that the user is entering a state of less-than-moderate pain, and to transmit the electronic activation signal to the automatically activated scent diffuser, thereby conditioning the user to associate said scent with reduced pain; and a user-activated scent diffuser that, upon activation by a user, diffuses the same scent which was previously diffused by the automatically activated scent diffuser.

* * * * *